United States Patent [19]
Gaster et al.

[11] Patent Number: 5,972,937
[45] Date of Patent: Oct. 26, 1999

[54] HETEROCYCLIC COMPOUNDS POSSESSING 5HT$_{2C}$ RECEPTOR ANTAGONIST ACTIVITY

[75] Inventors: Laramie Mary Gaster, Bishop's Stortford; Paul Adrian Wyman, Epping; Keith Raymond Mulholland, Harlow; David Thomas Davies, Ware, all of United Kingdom

[73] Assignee: SmithKline Beecham p.l.c., Brentford, United Kingdom

[21] Appl. No.: 08/875,507

[22] PCT Filed: Jan. 24, 1996

[86] PCT No.: PCT/EP96/00369

§ 371 Date: Sep. 16, 1997

§ 102(e) Date: Sep. 16, 1997

[87] PCT Pub. No.: WO96/23769

PCT Pub. Date: Aug. 8, 1996

[30]  Foreign Application Priority Data

Feb. 2, 1995 [GB] United Kingdom ............... 9502051
May 20, 1995 [GB] United Kingdom ............... 9510254

[51] Int. Cl.$^6$ ............... C07D 209/08; C07D 403/12; C07D 401/12; A61K 31/40
[52] U.S. Cl. ............... 514/235.2; 514/255; 514/256; 514/275; 514/310; 514/313; 514/339; 514/361; 514/362; 514/363; 514/372; 514/378; 514/383; 514/414; 514/415; 544/143; 544/144; 544/328; 544/331; 544/373; 544/405; 546/143; 546/162; 546/201; 546/278.1
[58] Field of Search ............... 514/255, 256, 514/275, 310, 235.2, 313, 339, 361, 362, 363, 372, 378, 383, 414, 415; 544/143, 328, 144, 331, 373, 405; 546/143, 162, 201, 278.1; 548/214, 490, 245, 491, 246, 465, 127, 467, 128, 134, 140, 255, 266.6

[56]  References Cited

U.S. PATENT DOCUMENTS 4,428,881  1/1984  Hedrich et al. .................... 548/491
5,322,951  6/1994  King et al. ...................... 548/312.1

FOREIGN PATENT DOCUMENTS

WO 94/04533  3/1994  WIPO .
WO 94/14801  7/1994  WIPO .
WO 94/22871  10/1994  WIPO .
WO 95/01976  1/1995  WIPO .
WO 95 21844  8/1995  WIPO .
WO 95/29177  11/1995  WIPO .
WO 96/02637  2/1996  WIPO .

OTHER PUBLICATIONS

I.T. Forbes, "5–Methyl–1–(3–pyridylcarbamoyl)–1, 2.3.5–tetrahydropyrrolo[2,3–f]indole: A Novel 5 HT$_{2C}$/5–HT$_{2B}$ Receptor Antagonist with Improved Affinity, Selectivity, and Oral Activity", (1995), J. Med. Chem., 38(14), pp. 2524–2530.

*Primary Examiner*—Mukund J. Shah
*Assistant Examiner*—Deepak R. Rao
*Attorney, Agent, or Firm*—Linda E. Hall; Stephen A. Venetianer; Charles M. Kinzig

[57]  ABSTRACT

The invention relates to heterocyclic families of compounds having pharmacological activity, in particular possessing 5HT$_{2C}$ receptor antagonist activity processes for their preparation, to compositions containing them and to their use in the treatment of CNS disorders.

11 Claims, No Drawings

HETEROCYCLIC COMPOUNDS POSSESSING 5HT$_{2C}$ RECEPTOR ANTAGONIST ACTIVITY

This application is a 371 of PCT/EP96/00369 filed Jan. 24, 1996.

This invention relates to compounds having pharmacological activity, processes for their preparation, to compositions containing them and to their use in the treatment of CNS disorders.

WO 95/01976 (SmithKline Beecham plc) describes indoline derivatives which are described as possessing 5HT$_{2C}$ receptor antagonist activity. A structurally distinct class of compounds has now been discovered, which have been found to have 5HT$_{2C}$ receptor antagonist activity. Certain compounds of the invention also exhibit 5HT$_{2B}$ antagonist activity. 5HT$_{2C/2B}$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

The present invention therefore provides, in a first aspect, a compound of formula (I) or a salt thereof:

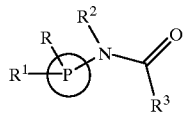
(I)

wherein:

P represents phenyl, a quinoline or isoquinoline residue, or a 5-membered or 6-membered aromatic heterocyclic ring containing up to three heteroatoms selected from nitrogen, oxygen or sulphur;

R is hydrogen, $C_{1-6}$ alkyl, $C_{2-6}$ alkenyl, $C_{2-6}$ alkynyl, $NR^4COR^5$, $C_{1-6}$ alkylthio, cyano, nitro, halogen, $CF_3$, $OCF_3$, $SCF_3$, $C_2F_5$, $NR^4R^5$, $CONR^4R^5$, CHO, $COR^6$, $CH_2OR^6$, $CO_2R^6$, $OR^6$ or $S(O)_nNR^4R^5$, where n is 1 or 2 and $R^4$, $R^5$ and $R^6$ are independently hydrogen, $C_{1-6}$ alkyl, aryl or aryl$C_{1-6}$ alkyl;

$R^1$ is hydrogen, $X(CR^8R^9)_pR^{10}$ where X is a bond, oxygen, sulphur, C=O, CH=N—O, $CONR^7$ or $NR^7$ where $R^7$ is hydrogen or $C_{1-6}$ alkyl; $R^8$ and $R^9$ are independently hydrogen or $C_{1-6}$ alkyl; p is 0 to 6 and $R^{10}$ is hydroxy, $C_{1-6}$ alkoxy, $NR^4R^5$ where $R^4$ and $R^5$ are as defined above for R, or $R^4$ and $R^5$ together form a $C_2$–$C_6$ methylene chain optionally containing an O, S or $NR^7$ group and optionally substituted by $NR^4R^5$ or $C_{1-6}$ alkyl$NR^4R^5$ where $R^4$ and $R^5$ are independently $C_{1-6}$ alkyl, or one of $R^4$ and $R^5$ represents an optionally substituted alicyclic amine attached directly or via a $C_{1-6}$ alkyl group, or $R^{10}$ is $CO_2R^{11}$ where $R^{11}$ is hydrogen, $C_{1-6}$ alkyl or aryl;

$R^2$ is hydrogen or $C_{1-6}$ alkyl;

$R^3$ is a group of formula (i):

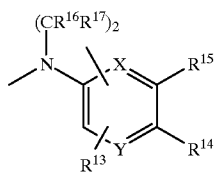
(i)

in which:

X and Y are both nitrogen, one is nitrogen and the other is carbon or a $CR^{12}$ group or one is a $CR^{12}$ group and the other is carbon or a $CR^{12}$ group;

$R^{12}$, $R^{13}$, $R^{14}$ and $R^{15}$ groups are independently hydrogen, $C_{1-6}$ alkyl optionally substituted by one or more halogen atoms, $C_{2-6}$ alkenyl, $C_{3-6}$ cycloalkyl, $C_{3-6}$ cycloalkyl$C_{1-6}$ alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$ alkoxy, hydroxy, halogen, nitro, $CF_3$, $C_2F_5$, $OCF_3$, $SCF_3$, $SO_2CF_3$, $SO_2F$, formyl, $C_{2-6}$ alkanoyl, cyano, optionally substituted phenyl or thienyl, $NR^4R^5$, $CONR^4R^5$ or $CO_2R^6$ where where $R^4$, $R^5$ and $R^6$ are as defined for $R^1$; or $R^{14}$ and $R^{15}$ form part of an optionally substituted 5- or 6-membered carbocyclic or heterocyclic ring;

$R^{16}$ and $R^{17}$ are independently hydrogen or $C_{1-6}$ alkyl; or $R^3$ is a group of formula (ii):

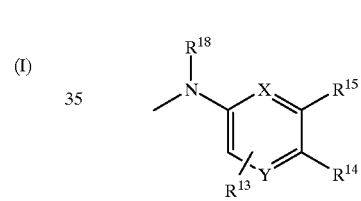
(ii)

in which X and Y are both nitrogen, one is nitrogen and the other is a $CR^{12}$ group or X and Y are both $CR^{12}$ groups, $R^{18}$ is hydrogen or $C_{1-6}$ alkyl, and $R^{12}$, $R^{13}$, $R^{14}$ and $R^{15}$ are as defined in formula (I); or $R^3$ is a group of formula (iii):

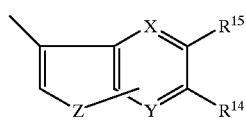
(iii)

in which $R^{14}$, $R^{15}$, X and Y are as defined in formula (i) and Z is O, S, $CH_2$ or $NR^{19}$ where $R^{19}$ is hydrogen or $C_{1-6}$ alkyl.

$C_{1-6}$ Alkyl groups, whether alone or as part of another group, may be straight chain or branched.

The urea moiety can be attached to a carbon or any available nitrogen atom of the ring P, preferably it is attached to a carbon atom. Suitable moieties when the ring P is a 5-membered aromatic heterocyclic rings include isothiazolyl, isoxazolyl, thiadiazolyl and triazolyl. Suitable moieties when the ring P is a 6-membered aromatic heterocyclic rings include, for example, pyridyl, pyrimidyl or pyrazinyl. When P is quinoline, or an isoquinoline residue, the urea moiety can be attached at any position of the ring, preferably to the 4- or 5-position. Preferably P is phenyl.

Suitably R is hydrogen, $C_{1-6}$ alkyl, $C_{2-6}$ alkenyl, $C_{2-6}$ alkynyl, $NR^4COR^5$, $C_{1-6}$ alkylthio, cyano, nitro, halogen, $CF_3$, $OCF_3$, $SCF_3$, $C_2F_5$, $NR^4R^5$, $CONR^4R^5$, CHO, $COR^6$, $CH_2OR^6$, $CO_2R^6$, $OR^6$ or $S(O)_nNR^4R^5$, where n is 1 or 2 and $R^4$, $R^5$ and $R^6$ are independently hydrogen, $C_{1-6}$ alkyl, aryl or aryl$C_{1-6}$ alkyl. Preferably R is hydrogen.

Suitably $R^1$ is hydrogen, $X(CR^8R^9)_pR^{10}$ where X is a bond, oxygen, sulphur, C=O, CH=N—O, $CONR^7$ or $NR^7$ where $R^7$ is hydrogen or $C_{1-6}$ alkyl; $R^8$ and $R^9$ are independently hydrogen or $C_{1-6}$ alkyl; p is 0 to 6 and $R^{10}$ is hydroxy, $C_{1-6}$ alkoxy, $NR^4R^5$ where $R^4$ and $R^5$ are as defined above for R or $R^4$ and $R^5$ together form a $C_2$–$C_6$ methylene chain optionally containing an O, S or $NR^7$ group and optionally substituted by $NR^4R^5$ or $C_{1-6}$ alkyl$^4R^5$ where $R^4$ and $R^5$ are independently $C_{1-6}$ alkyl, or one of $R^4$ and $R^5$ represents an optionally substituted alicyclic amine attached directly or via a $C_{1-6}$ alkyl group, or $R^{10}$ is $CO_2R^{11}$ where $R^{11}$ is hydrogen, $C_{1-6}$ alkyl or aryl. Preferably $R^1$ is $CO_2R^{11}$ where $R^{11}$ is hydrogen or $C_{1-6}$ alkyl, or $R^1$ is $X(CH_2)_pR^{10}$ where X is a bond, CONH or oxygen, p is 1 to 3, $R^{10}$ is OH or $NR^4R^5$ where $R^4$ and $R^5$ are $C_{1-6}$ alkyl, in particular methyl.

Preferably $R^2$ is hydrogen.

Preferably $R^3$ is a group of formula (i). Preferably $R^3$ is an indoline group having the following formula:

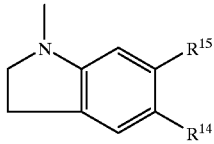

Suitably $R^{12}$, $R^{13}$, $R^{14}$ and $R^{15}$ groups are independently hydrogen, $C_{1-6}$ alkyl optionally substituted by one or more halogen atoms, $C_{2-6}$ alkenyl, $C_{3-6}$ cycloalkyl, $C_{3-6}$ cycloalkyl$C_{1-6}$ alkoxy, $C_{2-6}$ alkynyl, $C_{3-6}$ cycloalkyloxy, C3-6 cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, $CF_3$, $C_2F_5$, $OCF_3$, $SCF_3$, $SO_2CF_3$, $SO_2F$, formyl, $C_{2-6}$ alkanoyl, cyano, optionally substituted phenyl or thienyl, $NR^4R^5$, $CONR^4R^5$ or $CO_2R^6$ where where $R^4$, $R^5$ and $R^6$ are as defined for $R^1$; or $R^{14}$ and $R^{15}$ form part of an optionally substituted 5- or 6-membered carbocyclic or heterocyclic ring. Preferably $R^{12}$ and $R^{13}$ are both hydrogen.

Preferred $R^{14}$ and $R^{15}$ groups include $C_{1-6}$ alkyl, $C_{1-6}$alkoxy, $C_{1-6}$ alkylthio, halogen and $CF_3$. Most preferably $R^{14}$ is trifluoromethyl and $R^{15}$ is $C_{1-6}$alkoxy, in particular methoxy or $C_{1-6}$ alkylthio, in particular methylthio.

Particular compounds of the invention include:

5-Methoxy-6-trifluoromethyl-1-[3-(2-dimethylamino)-ethoxyphenyl-carbamoyl]indoline, 5-Methoxy-6-trifluoromethyl-1-[4-(2-dimethylamino)-ethoxyphenyl-carbamoyl]indoline, 5-Methylthio-6-trifluoromethyl-1-[3-(2-dimethylamino)-ethoxyphenyl-carbamoyl]indoline, 5-Methoxy-6-trifluoromethyl-1-[2-(2-dimethylamino)-ethoxyphenyl-carbamoyl]indoline, 5-Methylthio-6-trifluoromethyl-1-[3-(2-hydroxy)-ethoxyphenyl-carbamoyl]indoline, 5-Methylthio-6-trifluoromethyl-1-[3-ethoxycarbonylmethoxy)phenyl carbamoyl]indoline, 5-Methylthio-6-trifluoromethyl-1-[3-(3-hydroxypropyloxy)-phenyl-carbamoyl]indoline, 5-Methylthio-6-trifluoromethyl-1-[3-(2-dimethylaminoethyl)carbamoyl phenyl carbamoyl]indoline, 5-Methylthio-6-trifluoromethyl-1-[4-(2-dimethylaminoethyl)carbamoyl phenyl carbamoyl]indoline, 5-Methylthio-6-trifluoromethyl-1-(3-ethoxycarbonyl phenyl carbamoyl)indoline, 5-Methylthio-6-trifluoromethyl-1-(4-ethoxycarbonyl phenyl carbamoyl)indoline, 5-Methylthio-6-trifluoromethyl-1-(3-carboxy phenyl carbamoyl)indoline, 5-Methylthio-6-trifluoromethyl-1-(4-carboxy phenyl carbamoyl)indoline, 5-Methylthio-6-trifluoromethyl-1-[3-(2-methoxy) ethoxy phenyl carbamoyl]indoline, 5-Methylthio-6-trifluoromethyl-1-(3-ethoxyphenyl carbamoyl)indoline, 5-Methylthio-6-trifluoromethyl-1-[3-(2-hydroxyethyl) amidophenyl carbamoyl]indoline, 1-(3-(Dimethylaminomethyl)phenylcarbamoyl)-5-methylthio-6-trifluoromethylindoline, 1-[3-[(2-Aminoethyl)carbamoyl]phenylcarbamoyl]-5-methylthio-6-trifluoromethyl indoline, 1-[3-[2-Diethylaminoethyl)carbamoyl] phenylcarbamoyl]-5-methylthio-6-trifluoromethyl indoline, 1- [3-[(2-Diisopropylaminoethyl)carbamoyl] phenylcarbamoyl]-5-methylthio-6-trifluoromethyl indoline, 1-[3-[(2-Dibutylaminoethyl)carbamoyl] phenylcarbamoyl]-5-methylthio-6-trifluoromethyl indoline, 1-[3-[(2-Dimethylaminoethyl)methylcarbamoyl] phenylcarbamoyl]-5-methylthio-6-trifluoromethyl indoline, 1-[3-[(2-Dimethylaminopropyl)carbamoyl] phenylcarbamoyl]-5-methylthio-6-trifluoromethyl indoline, 1-[3-[(2-Pyridylmethyl)carbamoyl]phenylcarbamoyl]-5-methylthio-6-trifluoromethyl indoline, 1-[3-[(3-Dimethylamino-2-propyl)carbamoyl] phenylcarbamoyl]-5-methylthio-6-trifluoromethyl indoline, 1-[3-[(2-(N-Methyl-N-phenyl)ethyl)carbamoyl] phenylcarbamoyl]-5-methylthio-6-trifluoromethyl indoline, 1-[3-(4-Dimethylamino-1-oxobutyl)phenylcarbamoyl]-5-methylthio-6-trifluoromethyl indoline, 1-[3-(N-methylpiperazinylcarbonyl)phenylcarbamoyl]-5-methylthio-6-trifluoromethyl indoline, 1-[3-[(2-Piperid-1-ylethyl)carbamoyl]phenylcarbamoyl]-5-methylthio-6-trifluoromethyl indoline, 1-[3 [(2-Morpholin-4-ylethyl)carbamoyl] phenylcarbamoyl]-5-methylthio-6-trifluoromethyl indoline, 1-[3-[(N-Ethylpyrrolidin-2-ylmethyl)carbamoyl]phenyl carbamoyl]-5-methylthio-6-trifluoromethyl indoline, 1-[3-[(2-Pyrrolidin-1-ylethyl)carbarmoyl] phenylcarbamoyl]-5-methylthio-6-trifluoromethyl indoline, 1-[3-[(N-Benzylpyrrolidin-3-yl)carbamoyl] phenylcarbamoyl]-5-methylthio-6-trifluoromethyl indoline, 1-[3-[(2-Dimethylaminomethyl)pyrrolidin-1-yl) carbamoyl]phenyl carbamoyl]-5-methylthio-6-trifluoromethyl indoline, 1-[3-[(3-Dimethylaminopyrrolidin-1-yl)carbamoyl]
phenyl carbamoyl]-5-methylthio-6-trifluoromethyl
indoline,
1-[2-(Dimethylaminomethyl)phenylcarbamoyl]-5-
methoxy-6-trifluoromethyl indoline,
1-[2-(2-(Dimethylamino)ethyl)phenylcarbamoyl]-5-
methoxy-6-trifluoromethyl indoline,
1-[3-(2-(Dimethylamino)ethyl)phenylcarbamoyl]-5-
methoxy-6-trifluoromethyl indoline,
1-[3-(3-(Dimethylamino)propyl)phenylcarbamoyl]-5-
methoxy-6-trifluoromethyl indoline,
1-[3-[(2-Dimethylaminoethyl)carbamoyl]
phenylcarbamoyl]-5-methoxy-6-trifluoromethyl
indoline,
1-[4-(Dimethylaminomethyl)phenylcarbamoyl]-5-
methoxy-6-trifluoromethyl indoline,
1-[4-(2-(Dimethylamino)ethyl)phenylcarbamoyl]-5-
methoxy-6-trifluoromethyl indoline,
1-[3-(Dimethylaminomethyl)phenylcarbamoyl]-5-
methoxy-6-trifluoromethyl indoline,
1-[3-(3-(Dimethylamino)propyloxy)phenylcarbamoyl]-5-
methylthio-6-trifluoromethyl indoline,
1-[3-[(2-(Dimethylamino)ethyloxy)iminomethyl]
phenylcarbamoyl-5-methylthio-6-trifluoromethyl
indoline,
1-[Phenylcarbamoyl]-5-methylthio-6-trifluoromethyl
indoline,
1-(4-Hydroxymethylphenylcarbamoyl)-5-methylthio-6-
trifluoromethyl indoline,
1-[(5-Bromo-2-thienyl)carbamoyl]-5-methoxy-6-
trifluoromethyl indoline,
1-[2-Thienylcarbamoyl]-5-methoxy-6-trifluoromethyl
indoline,
and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form N-oxides or solvates such as hydrates, and the invention also extends to these forms. When referred to herein, it is understood that the term compound of formula (I)' also includes these forms.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:

the coupling of a compound of formula (II);

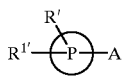

(II)

with a compound of formula (III);

B—R$^{3'}$ (III)

wherein P is as defined in formula (I), A and B contain the appropriate functional group(s) necessary to form the moiety —NR$^{2'}$CO when coupled, the variables R', R$^{1'}$ and R$^{3'}$ are R, R$^{1}$ and R$^{3}$ respectively, as defined in formula (I), or groups convertible thereto, and thereafter optionally and as necessary and in any appropriate order, converting any R', R$^{1'}$ and R$^{3'}$, when other than R, R$^{1}$ and R$^{3}$ respectively to R', R$^{1}$ and R$^{3}$, interconverting R, R$^{1}$ and R$^{3}$ and forming a pharmaceutically acceptable salt thereof.

The above reactions can be carried out using procedures well known in the art, for example those disclosed in WO 95/01976.

Compounds of formula (I) can be converted into other compounds of formula (I) using standard procedures. For example compounds where R$^{1'}$ forms an ethyl ester can be hydrolysed to the corresponding carboxylic acid which can then be converted to amide derivatives via acid chloride formation.

Pharmaceutically acceptable salts may be prepared conventionally by reaction with the appropriate acid or acid derivative. N-oxides may be formed conventionally by reaction with hydrogen peroxide or percarboxylic acids.

Compounds of formula (I) and their pharmaceutically acceptable salts have 5HT$_{2B/2C}$ receptor antagonist activity and are believed to be of potential use for the treatment or prophylaxis of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

DESCRIPTION 1

1-(2-Dimethylaminoethoxy)-3-nitrobenzene

To a stirred soluton of 3-nitrophenol (5 g, 36 mmol) in dimethylformamide (100 ml) at 0° C. was added sodium hydride (1.029 g, 80% dispersion in mineral oil, 34.3 mmol). After the effervescence had subsided 2-dimethylaminoethyl chloride was added (5.746 g, 37.8 mmol). After 1 hour the reaction mixture was allowed to warm to room temperature. After a further 2 hours the reaction mixture was heated to 70° C. for 14 hours, then evaporated under reduced pressure. The residue was then partitioned between water and ethyl acetate and the organic phase washed twice with aqueous sodium hydroxide solution (SM) and then saturated aqueous sodium chloride solution. Drying and evaporation gave the product as a brown oil (4.64 g, 61%)

$^1$H NMR (CDCl$_3$) δ: 7.65 (2H, m, J 7 Hz); 7.3 (1H, t, J 7 Hz); 7.1 (1H, d, J 7 Hz); 4.0 (2H, t, J 5 Hz); 2.7 (2H, t, J 5 Hz); 2.25 (6H, s).

DESCRIPTION 2

3-(2-Dimethylaninoethoxy)aniline

To a solution of 1-(2-dimethylaminoethoxy)-3-nitrobenzene (4.64 g, 22 mmol) in ethanol (200 ml) was added 10% palladium catalyst on charcoal (1 g). The reaction mixture was hydrogenated at atmospheric pressure for 2 hours, then filtered through kieselguhr and evaporated under reduced pressure to give the product as a yellow oil (4.0 g, 100%).

$^1$H NMR (CDCl$_3$) δ: 7.0 (1H, t, J 7 Hz); 6.25 (3H, m, J 7 Hz); 4.0 (2H, t, J 6 Hz); 3.7 (2H, s); 2.7 (2H, t, J 6 Hz); 2.3 (6H, s).

DESCRIPTION 3

1-(2-Dimethylaminoethoxy)-4-nitrobenzene

Prepared in the same manner as 1-(2-dimethylaminoethoxy)-3-nitrobenzene to yield the product as a yellow oil (0.58 g, 8%).

$^1$H NMR (CDCl$_3$) δ: 8.15 (2H, d, J 8 Hz); 6.95 (2H, d, J 8 Hz); 4.15 (2H, t, J 5 Hz); 2.75 (2H, t, J 5 Hz); 2.3 (6H, s).

DESCRIPTION 4

4-(2-Dimethylaminoethoxy)aniline

Prepared in the same manner as 1-(2-dimethylaminoethoxy)-3-nitrobenzene to yield the product as a yellow oil (0.43 g, 86%).

$^1$H NMR (CDCl$_3$) δ: 6.75 (2H, d, J 8 Hz); 6.6 (2H, d, J 8 Hz); 3.95 (2H, t, J 5 Hz); 3.4 (2H, s); 2.7 (2H, t, J 5 Hz); 2.3 (6H, s).

DESCRIPTION 5

1-(2-Dimethylamino)ethoxy-2-nitrobenzene

To a stirred solution of 2-nitrophenol (5 g, 36 mmol) in dimethylformamide (100 ml) was added potassium carbonate (9.94 g, 72 mmol) and 2-dimethylaminoethyl chloride hydrochloride (7.78 g, 54 mmol). This was then heated to 60° C. for 60 hours, then partitioned between half saturated aqueous sodium chloride and ethyl acetate. The organic phase was then washed four times with aqueous sodium hydroxide solution (5M), separated, dried and evaporated to give an orange solid. This was recrystallized from ethyl acetate affording the product as a yellow solid (1.43 g, 19%).

$^1$H NMR (CDCl$_3$) δ: 7.8 (1H, d, J 7 Hz), 7.5 (1H, t, J 6 Hz), 7.1 (1H, d, J 7 Hz), 7.0 (1H, t, J 6 Hz), 4.2 (2H, t, J 5 Hz), 2.8 (2H, t, J 5 Hz), 2.35 (6H, s)

DESCRIPTION 6

2-(2-Dimethylaminoethoxy)aniline

This was prepared in the same manner as 3-(2-Dimethylaminoethoxy)aniline to yield the product as a dark yellow oil (1.02 g, 83%).

$^1$H NMR (CDCl$_3$) δ: 6.65 (4H, m), 4.0 (2H, t, J 5 Hz), 3.85 (2H, s), 2.6 (2H, t, J 5 Hz), 2.2 (6H, s)

DESCRIPTION 7

1-t-Butyldimethylsilyloxy-2-iodoethane

A mixture of 2-iodoethanol (12.4 g, 72 mmol) and tert-butyldimethylsilyl chloride (11.94 g, 79 mmol) in chloroform (10 ml) was treated with imidazole (5.39 g, 79 mmol) which produced a white suspension. This was filtered and washed with chloroform. The filtrate was evaporated under reduced pressure to give the product as a colourless liquid (20.592 g, 100%).

¹H NMR (CDCl₃) δ: 3.7 (2H, t, J 6 Hz), 3.1 (2H, t, J 6 Hz), 0.8 (9H, s), 0.0 (6H, s)

DESCRIPTION 8

1-(2-t-Butyldimethylsilyloxyethoxy)-3-nitrobenzene

To a stirred solution of 3-nitrophenol (5 g, 36 mmol) in dimethylformamide (100 ml) at 0° C. was added sodium hydride (1.029 g, 34.4 mmol). After effervescence had subsided 1-t-butyldimethylsilyl-2-iodoethane was added (10.811 g, 37.8 mmol) and the reaction mixture left at room temperature for 18 hours. Potassium carbonate (2 g) was added and the mixture heated at 100° C. for 2 h. It was then quenched with saturated aqueous ammonium chloride solution and evaporated under reduced pressure. The residue was then partitioned between water and ethyl acetate and the organic extract washed with saturated aqueous sodium chloride solution twice, before being separated, dried, and evaporated under reduced pressure to give the crude product as a brown oil (9.697 g, 91%). This was chromatographed on silica eluting with 0–15% ethyl acetate/petroleum ether to give the product as a yellow oil (7.918 g, 74%)

¹H NMR (CDCl₃) δ: 7.7 (1H, d, J 7 Hz), 7.6 (1H, s), 7.3 (1H, t, J 8 Hz), 7.1 (1H, d, J 7 Hz), 4.0 (2H, t, J 5 Hz), 3.9 (2H, t, J 5 Hz), 0.8 (9H, s), 0.0 (6H, s).

DESCRIPTION 9

3-(2-t-Butyldimethylsilyloxyethoxy)aniline

To a solution of 1-(2-t-butyldimethylsilyloxyethoxy)-3-nitrobenzene (7.918 g, 27 mmol) in ethanol (150 ml) was added 10% palladium catalyst on charcoal (2 g) and the reaction mixture was hydrogenated at atmospheric pressure for 2 hours. It was then filtered through kieselguhr and evaporated under reduced pressure to yield the product as a yellow oil (6.707 g, 94%)

¹H NMR (CDCl₃) δ: 6.9 (1H, t, J 7 Hz), 6.15 (3H, m), 3.85 (4H, m), 3.5 (2H, s), 0.8 (9H, s), 0.0 (6H, s)

DESCRIPTION 10

5-Methylthio-6-trifluoromethyl-1-{3-[O-(2-tert-butyldimethyl-silyloxy)ethyl]phenylcarbamoyl}indoline To a stirred solution of carbonyldiimidazole (0.681 g, 4.2 mmol) in dichloromethane (10 ml) was added, dropwise, a solution of O-(2-tert-butyldimethylsilyloxy)ethyl-3-aminophenol (1.068 g, 4 mmol) in dichloromethane (10 ml). After 1 hour the reaction mixture was evaporated to dryness. The residue was then treated with 5-methylthio-6-trifluoromethyl indoline (0.933 g, 4 mmol) and dimethylformamide (10 ml) and heated to 100° C. for 1 hour. Water was added to give a white precipitate which was filtered to give the crude product as a white solid (1.576 g, 75%). This was then chromatographed on silica eluting with 0–5% ethyl acetate/petroleum ether to give the product as a white solid (0.705 mg, 34%).

¹H NMR (CDCl₃) δ: 8.2 (1H, s), 7.1 (1H, t, J 7 Hz), 7.0 (1H, s), 6.85 (1H, d, J 7 Hz), 6.55 (1H, s, J 7 Hz), 6.25 (1H, s), 4.0 (2H, t, J 7 Hz), 3.9 (4H, m), 3.2 (2H, t, J 7 Hz), 2.9 (3H, s), 0.8 (9H, s), 0.0 (6H, s)

DESCRIPTION 11

Ethyl(3-nitrophenoxy)acetate

This was made in the same manner as Description 1 to yield the product as a yellow oil (7.716 g, 95%).

¹H NMR (CDCl₃) δ: 7.8 (1H, d, J 7 Hz), 7.7 (1H, s), 7.4 (1H, t, J 7 Hz), 7.2 (1H, d, J 7 Hz), 4.7 (2H, s), 4.2 (2H, q, J 7 Hz), 1.2 (3H, t, J 7 Hz)

DESCRIPTION 12

Ethyl(3-aminophenoxy)acetate

This was made in the same manner as Description 2 to yield the product as a dark yellow oil (6.25 g, 93%)

¹H NMR (CDCl₃) δ: 7.0 (1H, t, J 7 Hz), 6.2 (3H, m), 4.5 (2H, s), 4.2 (2H, q, J 7 Hz), 3.7 (2H, s), 1.3 (3H, t, 7 Hz)

DESCRIPTION 13

1-(3-t-Butyldimethylsilyloxypropyloxy)-3-nitrobenzene

This was prepared in the same manner as Description 8 to yield the product as a yellow oil (5.5 g, 55%)

¹H NMR (CDCl₃) δ: 7.95 (1H, d, J 7 Hz), 7.9 (1H, s), 7.6 (1H, t, J 7 Hz), 7.4 (1H, d, J 7 Hz), 4.3 (2H, t, J 5 Hz), 4.0 (2H, t, J 5 Hz), 2.2 (2H, qn, J 5 Hz), 1.1 (9H, s), 0.0 (6H, s).

DESCRIPTION 14

3-(3-t-Butyldimethylsilyloxypropyloxy)aniline

This was prepared in the same manner as Description 9 to yield the product as a dark yellow oil (4.51 g, 91%)

¹H NMR (CDCl₃) δ: 7.05 (1H, t, J 7 Hz), 6.3 (3H, m), 4.0 (2H, t, J 5 Hz), 3.8 (2H, t, J 5 Hz), 3.7 (2H, s), 2.0 (2H, q), 0.9 (9H, s), 0.0 (6H, s).

DESCRIPTION 15

5-Methylthio-6-trifluoromethyl-1-[3-(3-tert-butyldimethylsilyloxy propyloxy)phenyl carbamoyl]indoline This was prepared in the same manner as 5-methylthio-6-trifluoromethyl-1-{3-[O-(2-tert-butyldimethylsilyloxy)ethyl]phenylcarbamoyl)}indoline to give the product as a white solid (0.85 g, 44%).

¹H NMR (CDCl₃) δ: 8.31 (1H, s), 7.2 (1H, t, J 7 Hz), 7.1 (1H, s), 6.9 (lH, d, J 7 Hz), 6.6 (1H, d, J 7 Hz), 6.3 (1H, s), 4.0 (4H, m), 3.75 (2H, t, J 5 Hz), 3.2 (2H, t, J 7 Hz), 2.4 (3H, s), 1.9 (2H, qn, J 5 Hz), 0.9 (9H, s), 0.0 (6H, s).

DESCRIPTION 16

6-Trifluoromethylindoline (D16)

6-Trifluoromethylindole[1] (5.27 g, 28.5 mmol) in glacial acetic acid (50 ml) was treated with sodium cyanoborohydride (3.60 g, 57.0 mmol) portionwise at room temperature with stirring. After 3 h at room temperature the reaction mixture was diluted with water (100 ml) and basified with 40% aqueous NaOH with cooling. The mixture was then extracted with dichloromethane (3×150 ml) and the combined extracts were dried (Na₂SO₄) and evaporated to give the title compound (4.83 g, 91%) as a brown solid.

NMR (CDCl₃) δ: 3.07 (2H, t), 3.62 (2H, t), 6.80 (1H, s), 6.92 (1H, d, J=8), 7.15 (1H, d, J=8).

1. A. N. Tischler and T. J. Lanza, *Tet. Lett.* 1986, 26, 1653.

DESCRIPTION 17

5-Thiocyanato-6-trifluoromethylindoline (D17)

A mixture of 6-trifluoromethylindoline (D 16) (9.7 g, 52 mmol) and potassium thiocyanate (10.09 g, 104 mmol) in methanol (200 ml) was treated with a solution of bromine (2.82 ml, 55 mmol) in methanol (35 ml) dropwise over 0.5 h at −5–0° C. The reaction mixture was allowed to warm to room temperature and stirred overnight then evaporated to dryness. The residue was partitioned between aqueous $K_2CO_3$ (100 ml) and dichloromethane (3×100 ml). The combined extracts were dried ($Na_2SO_4$) and evaporated and the residue chromatographed on silica using 2–30% ethyl acetate/petroleum ether as eluant to afford the title compound (9.1 g, 72%) as a yellow solid.

NMR ($CDCl_3$) δ: 3.12 (2H, t, J=8), 3.72 (3H, t, J=8), 4.23 (1H, br s), 6.89 (1H, s), 7.50 (1H, s).

DESCRIPTION 18

Di[5-(6-trifluoromethylindolinyl)]disulphide (D18)

The thiocyanate (D17) (28.5 g, 0.116 mol) in dioxane (200 ml) and water (100 ml) was treated with aqueous ammonia (880, 200 ml) at 90° C. for 1 h. The mixture was cooled and evaporated to give a residue which was partitioned between water (300 ml) and dichloromethane (4×300 ml). The combined extracts were dried ($Na_2SO_4$) and evaporated to give the title compound (25.5 g, 100%) as a yellow solid.

NMR($CDCl_3$) δ: 3.03 (2H, t, J=8), 3.67 (2H, t, J=8), 4.00 (1H, br s), 6.80 (1H, s), 7.49 (1H, s).

DESCRIPTION 19

Di-[5-(1-acetyl-6-trifluoromethylindolinyl)] disulphide (D19)

The disulphide (D18) (26 g, 0.119 mol) in dichloromethane (300 ml) and triethylamine (47.3 ml, 0.339 mol) was treated dropwise with a solution of acetic anhydride (22.5 ml, 0.238 mol) in dichloromethane (50 ml) at 0° C. The mixture was allowed to warm to room temperature, stirred for 1 h then poured into 2.5 M aqueous HCl (400 ml). The organic layer was separated and the aqueous was further extracted with dichloromethane (200 ml). The combined organic extracts were dried ($Na_2SO_4$) and evaporated to give the title compound (29.1 g, 94%) as a yellow solid.

NMR ($CDCl_3$) δ: 2.22 (3H, s), 3.21 (2H, t, J=8), 4.10 (2H, t, J=8), 7.68 (1H, s), 8.47 (1H, s).

DESCRIPTION 20

1-Acetyl-5-mercapto-6-trifluoromethylindoline (D20)

A mixture of the diacetyl disulphide (D19) (28.5 g, 54.8 mmol), triphenylphosphine (20.85 g, 79.5 mmol) and conc. aqueous HCl (1 ml) in dioxane (300 ml) and water (75 ml) was heated at reflux for 1.5 h. The reaction mixture was cooled and evaporated to a residue which was partitioned between dichloromethane (300 ml) and 1% aqueous NaOH (300 ml). The organic phase was further extracted with 1% aqueous NaOH (200 ml) and the combined aqueous fractions carefully acidified and extracted with dichloromethane (3×300 ml). The combined organic extracts were dried ($Na_2SO_4$) and evaporated to afford the title compound (26 g, 91%) as a yellow solid.

NMR ($CDCl_3$) δ: 2.24 (3H, s), 3.20 (2H, t, J=8), 3.68 (1H, m), 4.11 (2H, t, J=8), 7.22 (1H, s), 8.51 (1H, s).

DESCRIPTION 21

1-Acetyl-5-methylthio-6-trifluoromethylindoline (D21)

A mixture of the thiol (D20) (26 g, 99 mmol), anhydrous $K_2CO_3$ (15.12 g, 109 mmol) and iodomethane (18.6 ml, 300 mmol) in dry DMF (100 ml) was heated at 80° C. for 1 h. The reaction mixture was cooled, evaporated in vacuo and partitioned between water (200 ml) and dichloromethane (3×200 ml). The combined organics were washed with water (400 ml), dried ($Na_2SO_4$) and evaporated to yield the title compound (26.3 g, 97%) as a yellow oil.

NMR ($CDCl_3$) δ: 2.22 (3H, s), 2.49 (3H, s), 3.24 (2H, t, J=8), 4.12 (2H, t, J=8), 7.23 (1H, s), 8.51 (1H, s).

DESCRIPTION 22

5-Methylthio-6-trifluoromethylindoline (D22)

Method (a)

The acetyl indoline (D21) (26.3 g, 95 mmol) was treated with NaOH (30 g, 750 ml) in water (150 ml) and ethanol (200 ml) at reflux for 1.5 h. The reaction mixture was cooled, diluted with water (200 ml) and most of the ethanol evaporated in vacuo. The remaining mixture was extracted with dichloromethane (3×200 ml) and the combined extracts were dried ($Na_2SO_4$) and evaporated to afford the title compound (21.9 g, 99%) as a yellow oil.

NMR ($CDCl_3$) δ: 2.41 (3H, s), 3.07 (2H, t, J=8), 3.63 (2H, t, J=8), 3.90 (1H, br s), 6.88 (1H, s), 7.30 (1H, s).

Method (b)

A stirred solution of potassium thiocyanate (38.6 g, 0.39 mol) in methanol (470 ml) at −2° C. under argon was treated dropwise over 10 minutes with bromine (10.3 ml, 0.195 mol) giving a yellow precipitate. The reaction mixture was stirred at 0° C. for a further 15 minutes, then treated with a solution of 6-trifluoromethylindoline (D16) (33.2g, 0.177 mol) in methanol (320 ml) and allowed to warm to room temperature and stir for 4 h. A solution of potassium hydroxide (49.5 g, 0.88 mol) in water (300 ml) was added in one portion; causing temperature to rise to 43° C. and a brown solution to be produced. The mixture was stirred at 43–45° C. for 25 minutes, then cooled to 12° C. and treated with iodomethane (10.9 ml, 0.177 mol). The resulting mixture was allowed to warm to room temperature and stirred for 1.5 h, then concentrated in vacuo to approx. 350 ml volume. The residual aqueous mixture was extracted with dichloromethane (2×400 ml) and the combined extract dried ($Na_2SO_4$) and concentrated in vacuo to give a brown oil (43 g), which was chromatographed on silica gel eluting with dichloromethane to afford the title compound (D22) as a light brown solid (25.3 g, 61%) with spectral properties identical to those described above.

DESCRIPTION 23

N,N-Dimethyl-3-nitrobenzamide (D23)

3-Nitrobenzoyl chloride (1.03 g, 5.5 mmol) was treated with dimethylamine (40% aqueous solution) (5 ml). The reaction mixture was stirred under Argon for 2 hours, and then extracted with dichloromethane (70 ml). The organic extract was dried ($Na_2SO_4$) and concentrated in vacuo to afford the title compound as a pale yellow solid (0.94 g, 87%).

$^1$H NMR (200 MHz, $CDCl_3$) δ(ppm): 8.29 (m, 2H), 7.79 (m, 1H), 7.62 (m, 1H), 3.15 (s, 3H), 3.0 (s, 3H)

DESCRIPTION 24

N,N-Dimethyl-3-aminobenzamide (D24)

N,N-Dimethyl-3-nitrobenzamide (D23) (0.94 g, 4.8 mmol) was hydrogenated in ethanol (100 ml) over 10% Palladium-Charcoal (0.25 g) for 1 hour. The catalyst was removed by filtration through Kieselguhr, and the filtrate concentrated in vacuo to afford the title compound as a light brown solid (0.68 g, 87%).

$^1$H NMR (200 MHz, CDCl$_3$) δ(ppm): 7.15 (m, 1H), 6.70 (m, 3H), 3.75 (b, 2H), 3.09 (s, 3H), 2.95 (s, 3H)

DESCRIPTION 25

3-(N,N-Dimethylaminomethyl)aniline (D25)

A stirred suspension of lithium aluminium hydride (0.24 g, 6.3 mmol) in tetrahydrofuran (THF) (15 ml) at 0° C. under Argon, was treated dropwise over a period of fifteen minutes, with a solution of N,N-Dimethyl-3-aminobenzamide (D24) (0.68 g, 4.2 mmol) in THF (15 ml). The reaction mixture was allowed to warm to room temperature after which it was heated to reflux for 2 hours. The reaction mixture was allowed to cool to room temperature then treated sequentially with water (0.24 ml), 10% sodium hydroxide solution (0.24 ml) then water (0.72 ml). The reaction mixture was filtered through kieselguhr and the filtrate dried (Na$_2$SO$_4$) and concentrated in vacuo to afford the title compound as a pale brown oil (0.55 g, 87%).

$^1$H NMR (200 MHz, CDCl$_3$) δ(ppm): 0.10 (m, 1H), 6.62 (m, 3H), 3.24 (b, 2H), 3.32 (s, 2H), 2.22 (s, 6H).

DESCRIPTION 26

1-Methoxy-4-nitro-2-trifluoromethylbenzene (D26)

Sodium (11.78 g, 0.512 mol) was dissolved in dry methanol (1 l) and to the resulting solution was added a solution of 1-chloro-4-nitro-2-trifluoromethyl-benzene (96.22 g, 0.427 mol) in methanol (100 ml). The reaction mixture was refluxed for 3 h then cooled and evaporated in vacuo. The residue was partitioned between water (500 ml) and dichloromethane (3×400 ml). The combined organic extracts were dried (Na$_2$SO$_4$) and evaporated to give the title compound (93.76 g, 99%) as a white solid.

NMR (CDCl$_3$) δ: 4.05 (3H, s), 7.12 (1H, d, J=9), 8.45 (1H, dd, J=3,9), 8.52 (1H, d, J=3).

DESCRIPTION 27

(5-Methoxy-2-nitro-4-trifluoromethylphenyl) acetonitrile (D27)

A mixture of 1-methoxy-4-nitro 2-trifluoromethylbenzene (D26) (93 g, 0.421 mol) and 4-chlorophenoxyacetonitrile (77.55 g, 0.463 mol) in dry DMF (500 ml) was added dropwise over 0.75 h to a stirred solution of KO$^t$Bu (103.85 g, 0.927 mol) in dry DMF (400 ml) at −10° C. After complete addition the resulting purple solution was maintained at −10° C. for 1 h then poured into a mixture of ice/water (1.5 l) and 5 M aqueous HCl (1.5 l). The resulting mixture was extracted with dichloromethane (3×1 l). The combined extracts were washed with water (3 l), dried (Na$_2$SO$_4$) and evaporated under reduced pressure. The residue was chromatographed on silica using 10–40% ethyl acetate/petroleum ether as eluant to give the crude product which was recrystallised from ethyl acetate/petroleum ether to afford the title compound (85.13 g, 78%) as a white solid. Mp 103–104° C.

NMR (CDCl$_3$) δ: 4.10 (3H, s), 4.37 (2H, s), 7.34 (1H, s), 8.53 (1H, s).

DESCRIPTION 28

5-Methoxy-6-trifluoromethylindole (D28)

(5-Methoxy-2-nitro-4-trifluoromethylphenyl)acetonitrile (D27) (85g, 0.327 mol) in ethanol/water (9:1, 1.6l) and glacial acetic acid (16 ml) was hydrogenated over 10% palladium on carbon (50 g) at 50 psi for 0.5 h at room temperature. The reaction mixture was filtered and evaporated in vacuao. The residue was partitioned between aqueous K$_2$CO$_3$ (1 l) and dichloromethane (2×1 l) and the combined organic extract was dried (Na$_2$SO$_4$) and evaporated to afford the title indole (67.63 g, 96%) as a grey solid. NMR (CDCl$_3$) δ: 3.94 (3H, s), 6.53 (1H, m), 7.21 (1H, s), 7.32 (1H, m), 7.64 (1H, s), 8.25 (1H, br s).

DESCRIPTION 29

5-Methoxy-6-trifluoromethylindoline (D29)

The indole (D28) (67.63 g, 0.315 mol) was treated with sodium cyanoborohydride (40 g, 0.637 mol) in glacial acetic acid (500 ml) as in the method of Description 16 to afford the title indoline (67.73 g, 99%) as an off-white solid.

NMR (CDCl$_3$) δ: 3.07 (2H, t, J=8), 3.58 (2H, t, J=8), 3.67 (1H, br s), 3.83 (3H, s), 6.83 (1H, s), 6.88 (1H, s).

DESCRIPTION 30

3-Nitrobenzaldehyde oxime (D30)

3-Nitrobenzaldehyde (6 g, 40 mmol) was added to a solution of hydroxylamine (15 g, 216 mmol) in 5% aqueous sodium hydroxide solution (120 ml). Filtration and drying afforded the title compound as a white solid (5.23 g, 79%).

NMR (CDCl$_3$): 7.60 (1H, t), 7.80 (1H, s), 7.90 (1H, d), 8.20 (2H, m), 8.45 (1H, m)

DESCRIPTION 31

3-Nitrobenzaldehyde-O-dimethylaminopropyloxime (D31)

Sodium hydride (0.54 g of 80% dispersion in oil, 18.8 mmol) was added to oxime D30 (3 g, 18 mmol) at 0° C. in N,N-dimethylformamide (50 ml). After 0.25 h 3-dimethylaminopropyl chloride (2.13 g, 20 mmol) was added. The mixture was stirred at room temperature for 2 days then subjected to extractive workup and chromatography, affording the title oxime ether as a yellow oil (0.6 g, 15%).

NMR (CDCl$_3$): 2.30 (6H, s), 2.70 (2H, t), 4.30 (2H, t), 7.55 (1H, t), 7.90 (1H, d), 8.20 (2H, m), 8.55 (1H, m)

DESCRIPTION 32

3-Aminobenzaldehyde-O-dimethylaminopropyloxime (D32)

A solution of oxime ether D31 (0.3 g, 1.3 mmol) in ethanol (25 ml) was hydrogenated over platinum oxide (30 mg) for 0.5 h. Filtration and evaporation afforded the title aniline as a yellow oil (0.23 g, 88%).

NMR (CDCl$_3$): 2.30 (6H, s), 2.65 (2H, t), 3.70 (2H, bs), 4.25 (2H, t), 6.15 (1H, m), 6.90 (2H, m), 7.15 (1H, t), 8.05 (1H, s).

DESCRIPTION 33

2-[2-(Dimethylamino)ethyl]aniline (D33)

The title compound was prepared from 2-nitrophenylacetic acid by conversion to the N,N-dimethylamide, hydrogenation then reduction with lithium aluminium hydride.

EXAMPLE 1

5-Methoxy-6-trifluoromethyl-1-[3-(2-dimethylamino)-ethoxyphenyl-carbamoyl]indoline To a stirred solution of carbonyldiimidazole (0.28 g, 1.6 mmol) in dichloromethane (5 ml) was added, dropwsie over 5 minutes, a solution of 3-(2-dimethylaminoethoxy)aniline (0.288 g, 1.6 mmol) in dichloromethane (5 ml). After 1 hour the reaction mixture was evaporated to dryness under reduced pressure. The residue was then treated with 5-methoxy-6-trifluoromethyl indoline (0.35 g, 1.6 mmol) and dimethylformamide (20 ml) and heated to 100° C. for 1 hour. Water was added and the precipitate was filtered and dried to give the product as a white solid (0.35 g, 52%), m.p. 155–7° C.

$^1$H NMR (CDCl$_3$) δ: 8.2 (1H, s), 7.15 (2H, m), 6.9 (1H, d, J 7 Hz), 6.8 (1H, s), 6.65 (1H, d, J 7 Hz), 6.3 (1H, s), 4.05 (4H, m), 3.8 (3H, s), 3.25 (2H, t, J 8 Hz), 2.8 (2H, t, J 5 Hz), 2.3 (6H, s).

EXAMPLE 2

5-Methoxy-6-trifluoromethyl-1-[4-(2-dimethylamino)-ethoxyphenyl-carbamoyl]indoline Prepared in the same manner as 5-methoxy-6-trifluoromethyl-1-[3-(2-dimethylamino)-ethoxyphenyl-carbamoyl]indoline to give the product as a white crystalline solid (100 mg, 16%). m.p. 172–4° C.

$^1$H NMR (CDCl$_3$) δ: 8.2 (1H, s); 7.25 (2H, d, J 8 Hz); 6.9 (2H, d, J 8 Hz); 6.85 (1H, s); 6.25 (1H, s); 4.05 (4H, m); 3.85 (3H, s); 3.3 (2H, t, J 7 Hz); 2.7 (2H, t, 5 Hz); 2.3 (6H, s) m/e 423 C$_{21}$H$_{24}$F$_3$N$_3$O$_3$ requires 423

EXAMPLE 3

5-Methylthio-6-trifluoromethyl-1-[3-(2-dimethylamino)-ethoxyphenyl-carbamoyl]indoline This was produced in the same manner as 5-methoxy-6-trifluoromethyl-1-[3-(2-dimethylamino)-ethoxyphenyl-carbamoyl]indoline, using 5-methylthio-6-trifluoromethyl indoline in place of 5-methoxy-6-trifluoromethyl indoline, to yield the product as a brown solid (0.458 g, 65%), m.p. 155–7° C.

$^1$H NMR (CDCl$_3$) δ: 8.3 (1H, s); 7.2 (3H, m); 6.9 (1H, d, J 7 Hz); 6.7 (1H, d, J 7 Hz); 6.4 (1H, s); 4.1 (4H, m); 3.3 (2H, t, J 7 Hz); 2.7 (2H, t, J 5 Hz); 2.45 (3H, s); 2.3 (6H, s).

EXAMPLE 4

5-Methoxy-6-trifluoromethyl-1-[2-(2-dimethylamino)-ethoxyphenyl-carbamoyl]indoline This was prepared in the same manner as 5-methoxy-6-trifluoromethyl-1-[3-(2-dimethylamino) ethoxyphenyl carbamoyl]indoline to give the product as a white solid (0.196 g, 29%), m.p. 155–7° C.

$^1$H NMR (CDCl$_3$) δ: 8.25 (2H, m), 7.8 (1H, s), 6.95 (3H, m), 6.85 (1H, s), 4.15 (4H, m), 3.85 (3H, s), 3.3 (2H, t, J 7 Hz), 2.7 (2H, t, J 5 Hz), 2.3 (6H, s)

EXAMPLE 5

5-Thiomethyl-6-trifluoromethyl-1-[3-(2-hydroxy)-ethoxyphenyl-carbamoyl]indoline To a stirred solution of 5-thiomethyl-6-trifluoromethyl-1-{3-[O-(2-tert-butyldimethylsilyloxy)ethyl]phenyl carbamoyl}indoline (0.705 g, 1.34 mmol) in tetrahydrofuran (5 ml) was added tetra-n-butylammonium fluoride in tetrahydrofuran (1M) solution (2 ml, 2 mmol). After 1 hour saturated aqueous ammonium chloride solution was added and the reaction mixture partitioned between ethyl acetate/water. The organic extract was washed once with water and once with saturated aqueous sodium chloride solution before being dried with anhydrous sodium sulphate, filtered and evaporated under reduced pressure to give the product as a white solid (0.465 g, 86%), m.p. 155–6° C.

$^1$H NMR (DMSO) δ: 8.6 (1H, s), 8.2 (1H, s), 7.45 (1H, s), 7.25 (1H, s), 7.15 (2H, m), 6.6 (1H, d, J 5 Hz), 4.9 (1H, t, J 5 Hz), 4.2 (2H, t, J 7 Hz), 3.95 (2H, t, J 4 Hz), 3.7 (2H, q, J 4 Hz), 3.25 (2H, t, J 7 Hz), 2.5 (3H, s). m/e 412 C$_{19}$H$_{19}$F$_3$N$_2$O$_3$S requires 412

EXAMPLE 6

5-Methylthio-6-trifluoromethyl- 1-[3-ethoxycarbonylmethoxy) phenyl carbamoyl]indoline This was prepared in the same manner as 5-methoxy-6-trifluoromethyl-1-[3-(2-dimethylamino)-ethoxyphenylcarbamoyl]indoline to yield the product as a white solid (0.38 g, 16%) mp. 120–2° C.

$^1$H NMR (CDCl$_3$) δ: 8.3 (1H, s), 7.65 (3H, m), 6.9 (1H, d, J 7 Hz), 6.6 (1H, d, J 7 Hz), 6.4 (1H, s), 4.6 (2H, s), 4.25 (2H, q, J 7 Hz), 4.05 (2H, t, J 7 Hz), 3.25 (2H, t, J 7 Hz), 2.45 (3H, s), 1.3 (3H, t, J 7 Hz).
C$_{21}$H$_{21}$F$_3$N$_2$O$_4$S requires 454

EXAMPLE 7

5-Methylthio-6-trifluoromethyl-1-[3-(3-hydroxypropyloxy)-phenyl-carbamoyl]indoline This was prepared in the same manner as 5-methylthio-6-trifluoromethyl-1-[3-(2-hydroxy)-ethoxyphenyl-carbamoyl]indoline to give the product as a white solid (0.205 g, 31%) mp. 166–8° C.

$^1$H NMR (DMSO) δ: 8.55 (1H, s), 8.2 (1H, s), 7.45 (1H, s), 7.25 (1H, d, J 7 Hz), 7.15 (2H, m), 6.6 (1H, s), 4.5 (1H, t, J 5 Hz), 4.15 (2H, t, J 7 Hz), 3.95 (2H, t, J 5 Hz), 3.5 (2H, t, J 5 Hz), 3.3 (2H, t, J 7 Hz), 2.5 (3H, s), 1.8 (2H, qn, J 5 Hz) m/e=426

C$_{20}$H$_{21}$F$_3$N$_2$O$_3$S requires 426

EXAMPLE 8

5-Methylthio-6-trifluoromethyl-1-[3-[(2-dimethylaminoethyl)carbamoyl]phenyl carbamoyl] indoline To a suspension of 5-methylthio-6-trifluoromethyl-1-(3-carboxy phenyl carbamoyl) indoline (0.5 g, 1.26mmol) in dichloromethane (20 ml) was added oxalyl chloride (0.3 ml, 2.52 mmol) and dimethylformamide (3 drops). After effervescing had subsided the reaction mixture was evaporated to dryness under reduced pressure. It was then dissolved in tetrahydrofuran (30 ml) and added to a solution of N,N-dimethylethylenediamine (0.405 g, 6.33mmol) and triethylamine (0.2 ml, 1.4 mmol) in tetrahydrofuran at 0° C. After 2 hours the reaction mixture was basified with 5M NaOH and water was added forming a white precipitate. This was filtered and dried to give the product a white solid (0.25 g, 45%), m.p. 91–93° C.

$^1$H NMR (DMSO) δ 8.8(1H, s); 8.35 (1H, t, J 5 Hz); 8.2 (1H, s); 8.0 (1H, s); 7.75 (1H, d, J 7 Hz); 7.5 (3H, m); 7.4 (1H, t, J 7 Hz); 4.2 (2H, t, J 7 Hz); 3.3 (4H,t,J 7 Hz); 2.5 (3H,s); 2.4 (2H, t, J 7 Hz); 2.2 (6H, s). m/e=466 C$_{22}$H$_{25}$F$_3$N$_4$O$_2$5 requires 466

EXAMPLE 9

5-Methylthio-6-trifluoromethyl-1-[4-[(2-dimethylaminoethyl)carbamoyl]phenyl carbamoyl] indoline This was made in the same manner as 5-methylthio-6-trifluoromethyl-1-[3-(2-dimethylaminoethyl)carbamoyl phenyl carbamoyl]indoline to give the product as a white solid (0.22 g, 37%), m.p. 154–5° C.

¹H NMR (DMSO) δ=8.85(1H, s); 8.25 (1H, t, J 5 Hz); 8.2 (1H, s); 7.8 (2H, d, J 7 Hz); 7.7 (2H, d, J 7 Hz); 7.5 (1H, s); 4.2 (2H, t, J 7 Hz); 3.3 (4H, t, J 7 Hz); 2.5 (3H, s); 2.4 (2H, t, J 7 Hz); 2.2 (6H, s). m/e=466 $C_{22}H_{25}F_3N_4O_2S$ requires 466

EXAMPLE 10

5-Methylthio-6-trifluoromethyl-1-(3-ethoxycarbonyl phenyl carbamoyl)indoline

To a stirred solution of carbonyl diimidazole (1.782 g, 11 mmol) in dichloromethane (20 ml) was added dropwise a solution of ethyl 3-amino benzoate (1.65 g, 10 mml) in dichloromethane (20 ml). After 1 hour the reaction mixture was evaporated under reduced pressure before being treated with 5-methylthio-6-trifluoromethyl indoline (2.33 g, 10 mmol) and dimethylformamide (30 ml) and heated to 100° C. After 1 hour the reaction mixture was cooled and water added forming a yellow precipitate. This was filtered and dried to give the product as a yellow solid (4.19 g, 99%), m.p. 195–7° C.

¹H NMR (DMSO) δ: 8.85 (1H, s); 8.2 (2H, d, J 6 Hz); 7.9 (1H, d, J 7 Hz); 7.6 (1H, d, J 7 Hz); 7.4 (2H, t, J 6 Hz); 4.3 (2H, q, J 7 Hz); 4.2 (2H, t, J 8 Hz); 3.25 (2H, t, J 8 Hz); 2.5 (3H, s); 1.3 (3H, t, J 7 Hz).

EXAMPLE 11

5-Methylthio-6-trifluoromethyl-1-(4-ethoxycarbonyl phenyl carbamoyl)indoline

This was made in the same manner as 5-methylthio-6-trifluoromethyl-1-(3-ethoxycarbonyl phenyl carbamoyl) indoline using ethyl-4-amino benzoate to give the product as a yellow solid (3.948 g, 93%), m.p.>200° C.

¹H NMR (DMSO) δ: 8.95 (1H, s); 8.2 (1H, s); 7.9 (2H, d, J 7 Hz); 7.75 (2H, d, J 7 Hz); 7.4 (1H, s), 4.2 (4H, m); 3.25 (2H, t, J 8 Hz); 2.5 (3H, s); 1.3 (3H, t, J 7 Hz)

EXAMPLE 12

5-Methylthio-6-trifluoromethyl-1-(3-carboxy phenyl carbamoyl)indoline

To a suspension of 5-methylthio-6-trifluoromethyl-1-(3-ethoxy carbonyl phenyl carbamoyl)indoline (3g, 7.1 mmol) in ethanol (30 ml) was added aqueous sodium hydroxide solution (SM) (7.1 ml, 35.5 mmol) and heated gently for 2 hours. It was then allowed to cool and acidified with aqueous hydrochloric acid (5M) forming a white precipitate which was filtered and dried to yield the product as a white solid (2.324 g, 83%), mp>200° C.

¹H NMR (DMSO) δ: 12.95 (1H, s); 8.85 (1H, s); 8.2 (2H, s); 7.85 (1H, d, J 7 Hz); 7.6 (1H, d, J 7 Hz); 7.4 (2H, t, J 7 Hz); 4.2 (2H, t, J 6 Hz); 3.25 (2H, t, J 6Hz); 2.5 (3H, s)

EXAMPLE 13

5-Methylthio-6-trifluoromethyl-1-(4-carboxy phenyl carbamoyl)indoline

This was made in the same manner as 5-methylthio-6-trifluoromethyl-1-(3-carboxy phenyl carbamoyl)indoline using 5-methylthio-6-trifluoromethyl-1-(4-ethoxycarbonyl phenyl carbamoyl)indoline to give the product as a pale green solid (2.455 g, 88%), mp>200° C.

¹H NMR (DMSO) δ: 1.27 (1H, s); 8.9 (1H, s); 8.2 (1H, s); 7.9 (2H, d, J 7 Hz); 7.7 (2H, d, J 7 Hz); 7.4 (1H, s); 4.2 (2H, t, J 8 Hz); 3.75 (2H, t, J 8 Hz); 2.5 (3H, s)

EXAMPLE 14

5-Methylthio-6-trifluoromethyl-1-[3-(2-methoxy) ethoxy phenyl carbamoyl]indoline Prepared by the analogous routes as Example 1 (36%), m.p. 171–172.7° C.

EXAMPLE 15

5-Methylthio-6-trifluoromethyl-1-(3-ethoxyphenyl carbamoyl)indoline

Prepared by the reaction of 3-ethoxyphenyl isocyanate with 5-thiomethyl-6-trifluoromethyl indoline (22%), m.p. 233–4° C.

EXAMPLE 16

5-Methylthio-6-trifluoromethyl-1-[3-(2-hydroxyethyl) amidophenyl carbamoyl]indoline Prepared by an analogous route to Example 8 (52%), m.p. 215–215° C.

EXAMPLE 17

1-(3-(Dimethylaminomethyl)phenylcarbamoyl)-5-methylthio-6-trifluoromethylindoline A stirred solution of 1,1'Carbonyldiimidazole (0.65 g, 4.0 mmol) in dichloromethane (DCM) (60 ml) was treated with 3-N,N-Dimethylaminomethyl aniline (D25) (0.55 g, 3.6 mmol). The reaction mixture was stirred at room temperature for 0.5 hour, evaporated in vacuo, and then treated with 5-thiomethyl-6-trifluoromethyl indoline (D7) (0.85 g, 3.6 mmol) in N,N-dimethylformamide (15 ml). The reaction mixture was stirred at room temperature for 24 hours, after which it was slowly added to water (150 ml) and left to stand for 0.5 hour. It was then extracted with ethyl acetate (2×100 ml), followed by DCM (2×100 ml). The combined organic extracts were dried ($Na_2SO_4$) and concentrated in vacuo to afford a brown oil (1.93 g). This was chromatographed on silica gel eluting with 0 to 10% methanol/DCM affording the title compound as a white powder (0.16 g, 11%).

¹H NMR (200 MHz, d⁶DMSO) δ(ppm): 8.12 (s, 1H), 8.21 (s, 1H), 7.50 (m, 3H), 7.23 (t, 1H), 6.95 (d, 1H), 4.20 (t, 2H), 3.40 (s, 2H), 3.29 (t, 2H), 2.50 (s, 3H), 2.17 (s, 6H)

EXAMPLE 18

1-[3-[(2-Aminoethyl)carbamoyl]phenylcarbamoyl]-5-methylthio-6-trifluoromethyl indoline (E18)

The acid chloride was formed using the carboxylic acid from Example 12 (1.2 g, 3.1 mmol) and oxalyl chloride (0.72 ml, 8.1 mmol) in the usual way, dissolved in THF and added to a solution of tert-butyl N-(2-aminoethyl)-carbamate (0.5 g, 3.1 mmol) in THF to give the Boc-protected ethylene diamine (1.6 g, 100%). A portion of this (0.7 g, 1.3 mmol) in EtOAc was deprotected by bubbling HCl gas through the solution for 5 mins. Filtration afforded the title compound as a tan powder (0.44 g, 67%). M.pt. 175° C. (dec).

NMR 250 MHz, d⁶-DMSO δ: 8.90 (s, 1H), 8.71 (t, 1H), 8.21 (s, 1H), 8.10 (br, 3H), 7.75 (d, 1H), 7.62 (d, 1H), 7.45

(s, 1H), 7.40 (t, 1H), 4.25 (t, 2H), 3.54 (t, 2H), 3.25 (t, 1H), 2.98 (t, 2H), 2.50 (s, 3H). m/e 438, $C_{20}H_{21}F_3N_4O_2S$ requires 438.

EXAMPLE 19

1-[3-[2-Diethylaminoethyl)carbamoyl] phenylcarbamoyl]-5-methylthio-6-trifluoromethyl indoline (E19)

This was prepared in 8% yield by the same methodology as for Example 8, affording the product as a white solid. m.p. 76–8° C.

NMR (D6-DMSO): 1.00 (6H, t), 2.40–2.60 (6H, m), 2.50 (3H, s), 3.30 (4H, m), 4.20 (2H, t), 7.40 (1H, t), 7.50 (2H, m), 7.75 (1H, m), 8.05 (1H, s), 8.25 (1H, s), 8.35 (1H, t), 8.85 (1H, s).

EXAMPLE 20

1-[3-[(2-Diisopropylaminoethyl)carbamoyl] phenylcarbamoyl]-5-methylthio-6-trifluoromethyl indoline (E20)

This was prepared in 70% yield by the same method as for Example 8, affording the title compound as a white solid. m.p. 97–99° C.

NMR (D6-DMSO): 1.00 (12H, d), 2.50 (3H, s), 2.95 (2H, quintuplet), 3.30 (4H, m), 4.20 (2H, t), 7.35 (1H, t), 7.45 (2H, m), 7.75 (1H, d), 8.05 (1H, s), 8.25 (1H, s), 8.30 (1H, t), 8.80 (1H, s).

EXAMPLE 21

1-[3-[(2-Dibutylaminoethyl)carbamoyl] phenylcarbamoyl]-5-methylthio-6-trifluoromethyl indoline (E21)

This was prepared in 53% yield by the same method as for Example 8, affording the title compound as a white solid. m.p. 128–130° C.

NMR (D6-DMSO): 0.90 (6H, t), 1.20–1.40 (8H, m), 2.40 (4H, t), 2.50 (3H, s), 2.55 (2H, t), 3.30 (4H, m), 4.20 (2H, t), 7.35 (1H, t), 7.45 (2H, m), 7.75 (1H, d), 8.05 (1H, s), 8.25 (2H, m), 8.80 (1H, s).

EXAMPLE 22

1-[3-[(2-Dimethylaminoethyl)methylcarbamoyl] phenylcarbamoyl]-5-methylthio-6-trifluoromethyl indoline (E22)

The carboxylic acid from Example 12 (0.5 g, 1.25 mmol) in dichloromethane (10 ml) was treated with oxalyl chloride (0.3 ml, 3.4 mol) and DMF (catalytic). Solution was stirred for 1 h and evaporated to dryness. The residue in dry THF (5 ml) was added to a stirred solution of triethylamine (0.3 ml, 4 mmol) and N,N,N'-trimethylethylenediamine (0.5 ml, 4.5 mmol) in dry THF (10 ml). Following 3 hours at room temperature, the solution was partitioned ($H_2O$/EtOAc). Drying and removal of the organic layers followed by recrystallisation (EtOAc/60°–80° petrol) afforded the title compound (0.5 g, 83%) as a white solid. M.pt. 140°–141° C.

NMR 250 MHz, $CDCl_3$ δ: 8.30 (s, 1H), 7.47 (br, 2H), 7.30 (m, 1H), 7.10 (d, 1H), 6.86 (s, 1H), 4.15 (t, 2H), 3.65 (br, 1H), 3.30 (t, 2H), 3.05 (br d, 2H), 2.58 (br, 1H), 2.50 (s, 3H), 2.31 (s, 3H), 2.11 (s, 3H), 1.70 (s, 3H). Mass spec.

EXAMPLE 23

1-[3-[(2-Dimethylaminopropyl)carbamoyl] phenylcarbamoyl]-5-methylthio-6-trifluoromethyl indoline (E23)

This was prepared using the same methodology as for Example 8, affording the product as a white solid m.p. 86–8° C.

NMR (D6-DMSO): 1.65 (2H, quintuplet), 2.10 (6H, s), 2.25 (2H, t), 2.50 (3H, s), 3.30 (4H, m), 4.20 (2H, t), 7.35 (1H, t), 7.45 (2H, m), 7.75 (1H, d), 8.05 (1H, s), 8.25 (1H, s), 8.55 (1H, t), 8.85 (1H, s).

EXAMPLE 24

1-[3-[(2-Pyridylmethyl)carbamoyl] phenylcarbamoyl]-5-methylthio-6-trifluoromethyl indoline (E24)

This was prepared by the same method as for Example 8 affording the title compound in 54% yield as a white solid m.p. 116–8° C.

NMR (D6-DMSO): 2.50 (3H, s), 3.30 (2H, t), 4.20 (2H, t), 4.60 (2H, d), 7.20–7.40 (2H, m), 7.40–7.50 (2H, m), 7.60 (1H, d), 7.75 (2H, m), 8.05 (1H, s), 8.20 (1H, s), 8.50 (1H, d), 8.85 (1H, s), 9.10 (1H, t).

EXAMPLE 25

1-[3-[(3-Dimethylamino-2-propyl)carbamoyl] phenylcarbamoyl]-5-methylthio-6-trifluoromethyl indoline (E25)

This was prepared by a similar method to Example 8 affording the title compound in 66% yield as a white solid m.p. 86–88° C.

NMR (D6-DMSO): 1.10 (3H, d), 2.15 (6H, s), 2.30–2.50 (2H, m), 2.50 (3H, s), 3.30 (2H, t), 4.20 (3H, m), 7.40 (1H, t), 7.45 (2H, m), 7.75 (1H, d), 8.00 (1H, s), 8.15 (1H, d), 8.20 (1H, s), 8.80 (1H, s)

EXAMPLE 26

1-[3-[(2-(N-Methyl-N-phenyl)ethyl)carbamoyl] phenylcarbamoyl]-5-methylthio-6-trifluoromethyl indoline (E26)

This was prepared by similar methodology to Example 8 affording the title compound in 17% yield as a white solid, m.p. 88–90° C.

NMR (D6-DMSO): 2.50 (3H, s), 2.95 (3H, s), 3.30 (2H, t), 3.50 (4H, m), 4.20 (2H, t), 6.60 (1H, t), 6.85 (2H, d), 7.15 (2H, m), 7.35 (1H, t), 7.45 (2H, m), 7.75 (1H, d), 8.05 (1H, s), 8.20 (1H, s), 8.55 (1H, t), 8.80 (1H, s)

EXAMPLE 27

1-[3-(4-Dimethylamino-1-oxobutyl) phenylcarbamoyl]-5-methylthio-6-trifluoromethyl indoline (E27)

3-N,N-Dimethylaminopropylcarbonyl aniline* (0.81 g, 3.9 mmol) was reacted with phenyl chloroformate (0.54 ml, 4.3 mmol) and triethylamine (0.6 ml, 4.3 mmol) to form the carbamate. This was added to a solution of 5-methylthio-6-trifluoromethyl indoline (D22) (0.5 g of hydrochloride salt, 1.8 mmol) and triethylamine (0.25 ml, 1.8 mmol) in DMF (10 ml). The solution was heated to 120° C. for 24 hours and the evaporated to dryness. This residue was partitioned (EtOAc/$H_2O$). Organics were dried and removed in vacuo, the residue flash chromatographed (dichloromethane—20% MeOH/DCM) to afford the title compound (60 mg, 7%) as a yellow powder, M.pt. 178°–180° C.

*Prepared using methodology of Yamguchi, S and Kuninobu K, *Bull. Chem. Soc. JPN.* 50 (11), 3033–38, 1977.

NMR $CDCl_3$ 250 MHz δ: 8.32 (s, 1H), 8.07 (s, 1H), 7.93 (d, 1H), 7.62 (d, 1H), 7.38 (t, 1H), 7.25 (s, 1H), 4.25 (t, 2H), 3.30 (t, 2H), 3.12 (t, 2H), 2.82 (t, 2H), 2.60 (s, 6H), 2.50 (s,

3H), 2.10 (t, 2H). Mass spec m/z=466 (M⁺H)

EXAMPLE 28

1-[3-(N-methylpiperazinylcarbonyl) phenylcarbamoyl]-5-methylthio-6-trifluoromethyl indoline (E28)

The carboxylic acid from Example 12 (0.5 g, 1.25 mmol) in dichloromethane (10 ml) was treated with oxalyl chloride (0.3 ml, 3.4 mmol) and DMF (catalytic). The solution was stirred for 1 hour and evaporated to dryness. The residue in dry THF (5 ml) was added to a solution of triethylamine in dry (0.3 ml, 4 mmol) and N-Methyl piperazine (0.5 ml, 4.5 mmol) in THF (10 ml). After 3 hours of stirring the solution was partitioned (EtOAc/H$_2$O). Removal and drying of the solvent followed by rexst (EtOAc/60°–80° C. petrol) afforded the title compound as a white powder, m.pt. 220°–222° C.

NMR 250 MHz, CDCl$_3$ δ: 8.30 (s, 1H), 7.50 (d, 1H), 7.38 (s, 1H), 7.30 (m, 2H), 7.05 (m, 2H), 4.15 (t, 2H), 3.80 (br, 2H), 3.48 (br, 2H), 3.29 (t, 2H), 2.47 (s, 3H), 2.32 (br, 7H).

EXAMPLE 29

1-[3-[(2-Piperid-1-ylethyl)carbamoyl] phenylcarbamoyl]-5-methylthio-6-trifluoromethyl indoline (E29)

This was prepared by a similar method to Example 8, affording the title compound in 46% yield as a white solid, m.p. 79–81° C.

NMR (D6-DMSO): 1.50 (6H, m), 2.35 (4H, m), 2.45 (2H, t), 3.30 (2H, t), 3.40 (2H, t), 4.20 (2H, t), 7.35 (1H, t), 7.45 (1H, s), 7.75 (1H, d), 8.00 (1H, s), 8.20 (1H, s), 8.30 (1H, t), 8.80 (1H, s).

EXAMPLE 30

1-[3[(2-Morpholin-4-ylethyl)carbamoyl] phenylcarbamoyl]-5-methylthio-6-trifluoromethyl indoline (E30)

This was prepared by similar methodology to Example 8, affording the title compound in 50% yield as a white solid, m.p. 198–200° C.

NMR (D6-DMSO): 2.45 (6H, m), 2.50 (3H, s), 3.30 (2H, t), 3.40 (2H, t), 3.55 (4H, m), 4.20 (2H, t), 7.35 (1H, t), 7.45 (2H, m), 7.75 (1H, d), 8.05 (1H, s), 8.20 (1H, s), 8.35 (1H, t), 8.80 (1H, s).

EXAMPLE 31

1-[3-[(N-Ethylpyrrolidin-2-ylmethyl)carbamoyl] phenyl carbamoyl]-5-methylthio-6-trifluoromethyl indoline (E31)

The carboxylic acid from Example 12 (0.5 g, 1.25 mol) in dichloromethane (10 ml) was treated with oxalyl chloride (6.3 ml, 3.4 mmol) and DMF (catalytic). The solution was stirred for 1 hour and evaporated to dryness. The residue in dry THF (5 ml) was added to a stirred solution of triethylamine (0.3 ml, 4 mmol) and N-Ethyl-2-aminomethyl pyrrolidine (0.57 g, 4.5 mmol). After 3 hours at room temperature the solution was partitioned (EtOAc/H$_2$O). Drying and removal of organics followed by rexst (EtOAc/60°–80° C. petrol) afforded the title compound as a white powder, m.pt. 174°–175° C.

NMR 250 MHz CDCl$_3$ δ: 8.34 (s, 1H), 7.78 (m, 2H), 7.38 (m, 2H), 7.25 (s, 1H), 6.96 (br, 1H), 6.82 (s, 1H), 4.16 (m, 2H), 3.70 (m, 1H), 3.30 (m, 4H), 2.50 (s, 3H), 2.23 (m, 2H), 1.90 (m, 2H), 1.70 (m, 4H), 1.15 (t, 3H). Mass spec m/z=506 (M⁺)

EXAMPLE 32

1-[3-[(2-Pyrrolidin-1-ylethyl)carbamoyl] phenylcarbamoyl]-5-methylthio-6-trifluoromethyl indoline (E32)

This was prepared by similar methodology to Example 8, affording the title compound in 60% yield as a white solid, m.p. 91–93° C.

NMR (D6-DMSO): 1.65 (4H, m), 2.45 (4H, m), 2.50 (3H, s), 2.55 (2H, t), 3.20 (2H, t), 3.30 (2H, t), 4.20 (2H, t), 7.35 (1H, t), 7.45 (2H, m), 7.75 (1H, d), 8.05 (1H, s), 8.25 (1H, s), 8.40 (1H, t), 8.85 (1H, s).

EXAMPLE 33

1-[3-[(N-Benzyl pyrrolidin-3-yl)carbamoyl] phenylcarbamoyl]-5-methylthio-6-trifluoromethyl indoline (E33)

The carboxylic acid from Example 12 (0.5 g, 1.25 mmol) in dichloromethane (10 ml) was treated with oxalyl chloride (0.3 ml, 3.4 mmol) and DMF (catalytic). The solution was stirred for 1 hour and evaporated to dryness. The residue in dry THF (3 ml) was added to a stirred solution of triethylamine (0.3ml, 4 mmol) and 3-amino-N-benzyl pyrrolidine (0.79 g, 4.5 mmol) in dry THF (10 ml). Following 3 hours at room temperature the solution was partitioned (H$_2$O/EtOAc). Drying and removal of solvent followed by rexst (EtOAc/60°–80° C. petrol) afforded the title compound (0.62 g, 89%) as a white powder. M.pt. 174°–175° C.

NMR 250 MHz, CDCl$_3$ δ: 8.30 (s, 1H), 7.70 (m, 2H), 7.45–7.18 (m, 6H), 4.12 (br, 1H), 4.11 (m, 2H), 3.60 (s, 2H), 3.26 (t, 2H), 2.93 (m, 1H), 2.68 (m, 2H), 2.48 (s, 3H), 2.31 (m, 2H), 1.72 (m, 1H). Mass spec: m/z=554 (M⁺)

EXAMPLE 34

1-[3-[(2-Dimethylaminomethyl)pyrrolidin-1-yl) carbamoyl]phenyl carbamoyl]-5-methylthio-6-trifluoromethyl indoline (E34)

This was prepared using similar methodology to Example 8, affording the title compound in 31% yield as a white solid, m.p. 105°–7° C.

NMR (D6-DMSO): 1.80–2.00 (4H, m), 2.10 (6H, s), 2.20 (2H, m), 2.50 (3H, s), 3.25 (2H, t), 3.40 (2H, m), 4.20 (3H, m), 7.05 (1H, d), 7.30 (1H, t), 7.45 (1H, s), 7.60 (2H, m), 8.20 (1H, s), 8.55 (1H, bs).

EXAMPLE 35

1-[3-[(3-Dimethylaminopyrrolidin-1-yl)carbamoyl] phenyl carbamoyl]-5-methylthio-6-trifluoromethyl indoline (E35)

This was prepared using similar methodology as Example 8, affording the title compound in 43% yield as a white solid, m.p. 114–6° C.

NMR (D6-DMSO): 1.70 (1H, m), 2.05 (1H, m), 2.10 (3H, s), 2.15 (3H, s), 2.50 (3H, s), 2.60 (1H, m), 3.15–3.75 (6H, m), 4.20 (2H, t), 7.15 (1H, m), 7.35 (1H, t), 7.45 (1H, s), 7.65 (1H, m), 7.75 (1H, m), 8.20 (1H, s), 8.75 (1H, s).

EXAMPLE 36

1-[2-(Dimethylaminomethyl)phenylcarbamoyl]-5-methoxy-6-trifluoromethyl indoline (E36)

This was prepared using similar methodology to Example 17, affording the title compound in 70% yield as a white solid m.p.>200° C.

NMR (CDCl₃): 2.25 (6H, s), 3.20 (2H, t), 3.50 (2H, s), 3.85 (3H, s), 4.05 (2H, t), 6.85 (1H, s), 6.95 (1H, t), 7.05 (1H, d), 7.25 (1H, s), 7.30 (1H, d), 8.15 (1H, d), 8.30 (1H, s).

EXAMPLE 37

1-[2-(2-(Dimethylamino)ethyl)phenylcarbamoyl]-5-methoxy-6-trifluoromethyl indoline (E37)

This was prepared from the aniline D33 and 5-methoxy-6-trifluoromethyl indoline (D29) using the procedure of Example 1 affording the title compound in 19% yield as a pink crystalline solid. m.p. 166–168° C.

NMR (CDCl₃): 2.25 (6H, s), 2.60 (2H, m), 3.25 (2H, t), 3.85 (3H, s), 4.05 (2H, t), 6.85 (1H, s), 6.95–7.10 (2H, m), 7.15–7.30 (2H, m), 7.70 (1H, d), 8.20 (1H, s).

EXAMPLE 38

1-[3-(2-(Dimethylamino)ethyl)phenylcarbamoyl]-5-methoxy-6-trifluoromethyl indoline (E38)

This was prepared using similar methodology to Example 37, affording the title compound in 2% yield as a white solid m.p. 167–169° C.

NMR (CDCl₃): 2.30 (6H, s), 2.55 (2H, m), 2.80 (2H, m), 3.30 (2H, t), 4.15 (2H, t), 6.85 (1H, s), 6.95 (1H, m), 7.10–7.30 (4H, m), 8.25 (1H, s).

EXAMPLE 39

1-[3-(3-(Dimethylamino)propyl)phenylcarbamoyl]-5-methoxy-6-trifluoromethyl indoline (E39)

This was prepared using similar methodology to Example 37 affording the tittle compound in 27% yield as a white crystalline solid, m.p. 121–3° C.

NMR (CDCl₃): 1.70 (2H, m), 2.30 (6H, s), 2.40 (2H, t), 2.55 (2H, t), 3.20 (2H, t), 3.85 (3H, s), 4.05 (2H, t), 6.75 (1H, s), 6.85 (1H, d), 7.20 (2H, m), 7.40 (2H, m), 8.25 (1H, s).

EXAMPLE 40

1-[3-[(2-Dimethylaminoethyl)carbamoyl]phenylcarbamoyl]-5-methoxy-6-trifluoromethyl indoline (E40)

1-(3-Carboxyphenylcarbamoyl)-5-methoxy-6-trifluoromethyl indoline, which was prepared in analogous manner to Example 12 (0.31 g, 0.8 mmol) was dissolved in dichloromethane (10 ml) and treated with oxalyl chloride (0.19 ml, 2.2 mmol) and DMF (catalytic). The solution was stirred for 1 hour and evaporated to dryness. The residue in dry THF (5 ml) was added to a stirred solution of triethylamine (0.35 ml, 2.56 mmol) and N,N-dimethylethylenediamine (0.31 mml, 2.88 mmol) in dry THF. After 3 hours stirring, the solution was partitioned (EtOAc/H₂O). Drying and removal of the solvent followed by rexst of (EtOAc/PE 60°–80°) afforded the title compound as a white powder. M.pt. 159°–160° C. Mass spec/ m/z=451 (M⁺H)

EXAMPLE 41

1-[4-(Dimethylaminomethyl)phenylcarbamoyl]-5-methoxy-6-trifluoromethyl indoline (E41)

This was prepared in 59% yield using similar methodology to Example 36, affording the title compound as a white solid, m.p. 169–70° C.

NMR (CDCl₃): 2.10 (6H, s), 3.25 (2H, t), 3.30 (2H, s), 3.80 (3H, s), 4.15 (2H, t), 7.20 (3H, m), 7.50 (2H, d), 8.10 (1H, s), 8.50 (1H, s).

EXAMPLE 42

1-[4-(2-(Dimethylamino)ethyl)phenylcarbamoyl]-5-methoxy-6-trifluoromethyl indoline (E42)

This was prepared by the same method as for Example 37, affording the title compound in 6% yield as a white solid m.p. 181–184° C.

NMR (D6-DMSO): 2.15 (6H, s), 2.40 (2H, t), 2.65 (2H, t), 3.25 (2H, t), 3.80 (3H, s), 4.20 (2H, t), 7.10 (2H, d), 7.20 (1H, s), 7.45 (2H, d), 8.10 (1H, s), 8.50 (1H, s)

EXAMPLE 43

1-[3-(Dimethylaminomethyl)phenylcarbamoyl]-5-methoxy-6-trifluoromethyl indoline (E43)

This was prepared by similar methodology to Example 36 affording the title compound in 19% yield as a white crystalline solid m.p. 134–40° C.

NMR (CDCl₃): 2.50 (6H, s), 3.25 (2H, t), 3.75 (2H, s), 3.85 (3H, s), 4.15 (2H, t), 6.85 (1H, s), 6.95 (1H, s), 7.05 (1H, d), 7.30 (1H, d), 7.65 (2H, m), 8.25 (1H, s).

EXAMPLE 44

1-[3-(3-(Dimethylamino)propyloxy)phenylcarbamoyl]-5-methylthio-6-trifluoromethyl indoline (E44)

This was prepared using similar methodology to Example 8, affording the title compound in 14% yield as a white solid. m.p. 149–151° C.

NMR (D6-DMSO): 1.85 (2H, quintuplet), 2.15 (6H, s), 2.35 (2H, t), 2.50 (3H, s), 3.24 (2H, t), 3.95 (2H, t), 4.20 (2H, t), 6.60 (1H, m), 7.15 (1H, s), 7.15–7.25 (2H, m), 7.55 (1H, s), 8.20 (1H, s), 8.55 (1H, s).

EXAMPLE 45

1-[3-[(2-(Dimethylamino)ethyloxy)iminomethyl]phenylcarbamoyl-5-methylthio-6-trifluoromethyl indoline (E45)

This was prepared from aniline D32 using the same methodology as for Example 27 affording the title compound in 64% yield as a white solid m.p.>250° C.

NMR (D6-DMSO): 2.10 (6H, s), 2.50 (3H, s), 3.30 (6H, m), 4.20 (2H, t), 7.25 (1H, d), 7.35 (1H, t), 7.65 (1H, d), 7.85 (1H, s), 8.25 (2H, s), 8.80 (1H, s).

EXAMPLE 46

1-[Phenylcarbamoyl]-5-methylthio-6-trifluoromethyl indoline (E46)

This was prepared from phenyl isocyanate and 5-methylthio-6-trifluoromethyl indoline in 34% yield m.p. 163–165° C.

NMR (CDCl₃): 2.50 (3H, s), 3.30 (2H, t), 4.15 (2H, t), 6.40 (1H, bs), 7.10 (1H, t), 7.25 (1H, s), 7.35 (1H, t), 7.40–7.50 (3H, m), 8.35 (1H, s).

EXAMPLE 47

1-(4-Hydroxymethylphenylcarbamoyl)-5-methylthio-6-trifluoromethyl indoline

4-Aminobenzyl alcohol was converted to the phenyl carbamate and treated with 5-methoxy-6-trifluoromethyl indoline as in the method of Example 27. Chromatography using ethyl acetate as eluant gave the title compound as a white crystalline solid. m.p. 184–7° C.

$^1$H NMR (250 MHz; DMSO) δ: 3.28 (2H, t, J 8 Hz), 3.37 (3H, s), 4.19 (2H, t, J 8 Hz), 4.45 (2H, br s), 5.11 (1H, br), 7.23 (2H, d, J 7 Hz), 7.46 (1H, s), 7.51 (1H, d, J 7 Hz), 8.22 (1H, s), 8.62 (1H, s)

EXAMPLE 48

1-[(5-Bromo-2-thienyl)carbamoyl]-5-methoxy-6-trifluoromethyl indoline (E48)

This was prepared from 5-bromo-thiophene-2-carboxylic acid in 78% via acyl azide formation and Curtius rearrangement to form the isocyanate and then treatment with 5-methoxy-6-trifluoromethyl indoline (D29).

NMR (D6-DMSO): 3.30 (2H, t), 3.85 (3H, s), 4.10 (2H, t), 6.55 (1H, d), 6.95 (1H, d), 7.20 (1H, s), 8.10 (1H, s), 10.10 (1H, s).

EXAMPLE 49

1-[2-Thienylcarbamoyl]-5-methoxy-6-trifluoromethyl indoline (E48)

A mixture of 5-methoxy-6-trifluoromethyl-1-(5-bromo-2-thienyl) carbamoyl indoline (E48) (0.64 g, 1.5 mmol), sodium carbonate (1.1 g), pyridine-3-boronic acid (0.55 g, 4.5 mmol) and tetrakis triphenylphine palladium(0) (0.1 g) in dimethoxyethane/water (20 ml/5 ml) was heated to reflux overnight under argon. Extraction workup and chromatography afforded the title compound in 27% yield as a white solid, m.p. 240–244° C.

NMR (D6-DMSO): 3.30 (2H, t), 3.85 (3H, s), 4.15 (2H, t), 6.75 (1H, m), 6.85 (1H, m), 6.90 (1H, m), 7.20 (1H, s), 8.15 (1H, s), 9.80 (1H, s).

Pharmacological data

[$^3$H]-mesulergine binding to rat or human 5-HT$_{2C}$ clones expressed in 293 cells in vitro Compounds were tested following the procedure outlined in WO 94/04533. The compounds of examples 1 to 49 have pKi values of 6.0 to 9.2.

Reversal of MCPP-induced Hypolocomotion

Compounds were tested following the procedure outlined in WO 94/04533. The compound of example 8 has an ID$_{50}$ of 10.0 mg/kg p.o.

We claim:

1. A compound of formula (I) or a salt thereof:

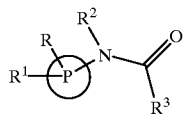

(I)

wherein:

P represents phenyl, a quinoline or isoquinoline residue, or a isothiazolyl, isoxazolyl, thiadiazolyl, triazolyl, pyridyl, pyrimidyl or pyrazinyl ring;

R is hydrogen, $C_{1-6}$ alkyl, $C_{2-6}$ alkenyl, $C_{2-6}$ alkynyl, NR$^4$COR$^5$, $C_{1-6}$ alkylthio, cyano, nitro, halogen, CF$_3$, OCF$_3$, SCF$_3$, C$_2$F$_5$, NR$^4$R$^5$, CONR$^4$R$^5$, CHO, COR$^6$, CH$_2$OR$^6$, CO$_2$R$^6$, OR$^6$ or S(O)$_n$NR$^4$R$^5$, where n is 1 or 2 and R$^4$, R$^5$ and R$^6$ are independently hydrogen, $C_{1-6}$ alkyl, aryl or arylC$_{1-6}$ alkyl;

R$^1$ is X(CR$^8$R$^9$)$_p$R$^{10}$ where X is a bond, oxygen, sulphur, C═O, CH═N—O, CONR$^7$ or NR$^7$ where R$^7$ is hydrogen or $C_{1-6}$ alkyl; R$^8$ and R$^9$ are independently hydrogen or $C_{1-6}$ alkyl; p is 1 to 6 and R$^{10}$ is hydroxy, $C_{1-6}$ alkoxy, NR$^4$R$^5$ where R$^4$ and R$^5$ are as defined above for R, or R$^4$ and R$^5$ together form a C$_2$–C$_6$ methylene chain optionally containing an O, S or NR$^7$ group and optionally substituted by NR$^4$R$^5$ or $C_{1-6}$ alkylNR$^4$R$^5$ where R$^4$ and R$^5$ are independently $C_{1-6}$ alkyl, or one of R$^4$ and R$^5$ represents an optionally substituted alicyclic amine attached directly or via a $C_{1-6}$ alkyl group, or R$^1$ is CO$_2$R$^{11}$ where R$^{11}$ is hydrogen, $C_{1-6}$ alkyl or aryl;

R$^2$ is hydrogen or $C_{1-6}$ alkyl;

R$^3$ is a group of formula (i):

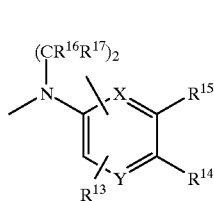

(i)

in which:

one of X or Y is a CR$^{12}$ group and the other is carbon;

R$^{12}$, R$^{13}$, R$^{14}$ and R$^{15}$ groups are independently hydrogen, $C_{1-6}$ alkyl optionally substituted by one or more halogen atoms, $C_{2-6}$ alkenyl, $C_{3-6}$ cycloalkyl, $C_{3-6}$ cycloalkylC$_{1-6}$alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, CF$_3$, C$_2$F$_5$, OCF$_3$, SCF$_3$, SO$_2$CF$_3$, SO$_2$F$_3$, SO$_2$F, formyl, $C_{2-6}$ alkanoyl, cyano, optionally substituted phenyl or thienyl, NR$^4$R$^5$, CONR$^4$R$^5$ or CO$_2$R$^6$ where R$^4$, R$^5$ and R$^6$ are as defined for R$^1$; or R$^{14}$ and R$^{15}$ form part of an optionally substituted 5- or 6-membered carbocyclic or heterocyclic ring; and R$^{16}$ and R$^{17}$ are independently hydrogen or $C_{1-6}$ alkyl.

2. A compound according to claim 1 in which R$^1$ is CO$_2$R$^{11}$ where R$^{11}$ is hydrogen or $C_{1-6}$ alkyl, or R$^1$ is X(CH$_2$)$_p$R$^{10}$ where X is a bond, CONH or oxygen, p is 1 to 3, and R$^{10}$ is OH or NR$^4$R$^5$ where R$^4$ and R$^5$ are $C_{1-6}$ alkyl.

3. A compound according to claim 2 in which R$^2$ is hydrogen.

4. A compound according to claim 3 in which R$^3$ is an indoline group having the following formula:

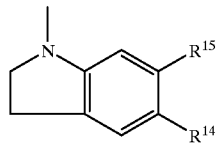

5. A compound according to claim 4 in which P is phenyl.

6. A compound according to claim 1 which is:

5-Methoxy-6-trifluoromethyl-1-[3-(2-dimethylamino)-ethoxyphenyl-carbamoyl]indoline, 5-Methoxy-6-trifluoromethyl-1-[4-(2-dimethylamino)-ethoxyphenyl-carbamoyl]indoline, 5-Methylthio-6-trifluoromethyl-1-[3-(2-dimethylamino)-ethoxyphenyl-carbamoyl]indoline, 5-Methoxy-6-trifluoromethyl-1 -[2-(2-dimethylamino)-ethoxyphenyl-carbamoyl]indoline, 5-Methylthio-6-trifluoromethyl-1-[3-(2-hydroxy)-ethoxyphenyl-carbamoyl]indoline, 5-Methylthio-6-trifluoromethyl-1-[3-ethoxycarbonylmethoxy)phenyl carbamoyl]indoline, 5-Methylthio-6-trifluoromethyl-1-[3-(3-hydroxypropyloxy)-phenyl-carbamoyl]indoline, 5-Methylthio-6-trifluoromethyl-1-[3-(2-dimethylaminoethyl)carbamoyl phenyl carbamoyl]indoline, 5-Methylthio-6-trifluoromethyl-1-[4-(2-dimethylaminoethyl)carbamoyl phenyl carbamoyl]indoline, 5-Methylthio-6-trifluoromethyl-1-(3-ethoxycarbonyl phenyl carbamoyl)indoline, 5-Methylthio-6-trifluoromethyl-1-(4-ethoxycarbonyl phenyl carbamoyl)indoline, 5-Methylthio-6-trifluoromethyl-1-(3-carboxy phenyl carbamoyl)indoline, 5-Methylthio-6-trifluoromethyl-1-(4-carboxy phenyl carbamoyl)indoline, 5-Methylthio-6-trifluoromethyl-1-[3-(2-methoxy)ethoxy phenyl carbamoyl]indoline, 5-Methylthio-6-trifluoromethyl-1-[3-(2-hydroxyethyl) amidophenyl carbamoyl]indoline, 1 -(3-(Dimethylaminomethyl)phenylcarbamoyl)-5-methylthio-6-trifluoromethylindoline, 1- [3-[(2-Aminoethyl)carbamoyl]phenylcarbamoyl]-5-methylthio-6-trifluoromethyl indoline, 1-[3-[2-Diethylaminoethyl)carbamoyl] phenylcarbamoyl]-5-methylthio-6-trifluoromethyl indoline, 1-[3-[(2-Diisopropylaminoethyl)carbamoyl] phenylcarbamoyl]-5-methylthio-6-trifluoromethyl indoline, 1-[3-[(2-Dibutylaminoethyl)carbamoyl] phenylcarbamoyl]-5-methylthio-6-trifluoromethyl indoline, 1-[3-[(2-Dimethylaminoethyl)methylcarbamoyl] phenylcarbamoyl]-5-methylthio-6-trifluoromethyl indoline, 1-[3-[(2-Dimethylaminopropyl)carbamoyl] phenylcarbamoyl]-5-methylthio-6-trifluoromethyl indoline, 1-[3-[(2-Pyridylmethyl)carbamoyl]phenylcarbamoyl]-5-methylthio-6-trifluoromethyl indoline, 1-[3-[(3-Dimethylamino-2-propyl)carbamoyl] phenylcarbamoyl]-5-methylthio-6-trifluoromethyl indoline, 1-[3-[(2-(N-Methyl-N-phenyl)ethyl)carbamoyl] phenylcarbamoyl]-5-methylthio-6-trifluoromethyl indoline, 1-[3-(4-Dimethylamino-1-oxobutyl)phenylcarbamoyl]-5-methylthio-6-trifluoromethyl indoline, 1-[3-(N-methylpiperazinylcarbonyl)phenylcarbamoyl]-5-methylthio-6-trifluoromethyl indoline, 1-[3-[(2-Piperid-1-ylethyl)carbamoyl]phenylcarbamoyl]-5-methylthio-6-trifluoromethyl indoline, 1-[3[(2-Morpholin-4-ylethyl)carbamoyl] phenylcarbamoyl]-5-methylthio-6-trifluoromethyl indoline, 1-[3-[(N-Ethylpyrrolidin-2-ylmethyl)carbamoyl]phenyl carbamoyl]-5-methylthio-6-trifluoromethyl indoline, 1-[3-[(2-Pyrrolidin-1-ylethyl)carbamoyl] phenylcarbamoyl]-5-methylthio-6-trifluoromethyl indoline, 1-[3-[(N-Benzylpyrrolidin-3-yl)carbamoyl] phenylcarbamoyl]-5-methylthio-6-trifluoromethyl indoline, 1-[3-[(2-Dimethylaminomethyl)pyrrolidin-1-yl) carbamoyl]phenyl carbamoyl]-5-methylthio-6-trifluoromethyl indoline, 1-[3-[(3-Dimethylaminopyrrolidin-1-yl)carbamoyl] phenyl carbamoyl]-5-methylthio-6-trifluoromethyl indoline, 1-[2-(Dimethylaminomethyl)phenylcarbamoyl]-5-methoxy-6-trifluoromethyl indoline, 1-[2-(2-(Dimethylamino)ethyl)phenylcarbamoyl]-5-methoxy-6-trifluoromethyl indoline, 1-[3-(2-(Dimethylamino)ethyl)phenylcarbamoyl]-5-methoxy-6-trifluoromethyl indoline, 1-[3-(3-(Dimethylamino)propyl)phenylcarbamoyl]-5-methoxy-6-trifluoromethyl indoline, 1-[3-[(2-Dimethylaminoethyl)carbamoyl] phenylcarbamoyl]-5-methoxy-6-trifluoromethyl indoline, 1-[4-(Dimethylaminomethyl)phenylcarbamoyl]-5-methoxy-6-trifluoromethyl indoline, 1-[4-(2-(Dimethylamino)ethyl)phenylcarbamoyl]-5-methoxy-6-trifluoromethyl indoline, 1-[3-(Dimethylaminomethyl)phenylcarbarmoyl]-5-methoxy-6-trifluoromethyl indoline, 1-[3-(3-(Dimethylamino)propyloxy)phenylcarbamoyl]-5-methylthio-6-trifluoromethyl indoline, 1-[3-[(2-(Dimethylamino)ethyloxy)iminomethyl] phenylcarbamoyl-5-methylthio-6-trifluoromethyl indoline, 1-(4-Hydroxymethylphenylcarbamoyl)-5-methylthio-6-trifluoromethyl indoline, and pharmaceutically acceptable salts thereof.

7. A process for the preparation of a compound of claim 1 or a pharmaceutically acceptable salt thereof, which process comprises:

the coupling of a compound of formula (II);

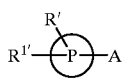 (II)

with a compound of formula (III);

 (III)

wherein P is as defined in formula (I), A and B contain the appropriate functional group(s) necessary to form the moiety —NR²CO when coupled, the variables R', R¹' and R³' are R, R¹ and R³ respectively, as defined in formula (I), or groups convertible thereto, and thereafter optionally and as necessary and in any appropriate order, converting any R', R¹' and R³', when other than R, R¹ and R³ respectively to R', R¹ and R³, interconverting R, R¹ and R³ and forming a pharmaceutically acceptable salt thereof.

8. A pharmaceutical composition which comprises a therapeutically effective amount of a compound according to claim 1 and a pharmaceutically acceptable carrier or excipient.

9. A method of antagonizing $5HT_{2C}$ receptors by administering to patient in need thereof, a compound of claim 1.

10. A method of treating CNS disorders by administering to a patient in need thereof, a compound of claim 1.

11. A method of treating anxiety or depression by administering to a patient in need thereof, a compound of claim 1.

* * * * *